United States Patent
Cao et al.

(10) Patent No.: US 11,891,401 B2
(45) Date of Patent: Feb. 6, 2024

(54) SOLID FORMS OF N-(4-FLUORO-3-(6-(3-METHYLPYRIDIN-2-YL)-[1,2,4]TRIAZOLO[1,5-A]PYRIMIDIN-2-YL)PHENYL)-2,4-DIMETHYLOXAZOLE-5-CARBOXAMIDE

(71) Applicant: NOVARTIS AG, Basel (CH)

(72) Inventors: Yudong Cao, Changshu (CN); Siyi Jiang, Shanghai (CN); Hongyong Kim, Changshu (CN); Andreas Kordikowski, Binningen (CH); Irene Xia, Pudong (CN); Bo Yu, Changshu (CN); Jing Zhang, Changshu (CN); Yi Zhao, Changshu (CN)

(73) Assignee: NOVARTIS AG, Basel (CH)

( * ) Notice: Subject to any disclaimer, the term of this patent is extended or adjusted under 35 U.S.C. 154(b) by 272 days.

(21) Appl. No.: 17/281,528

(22) PCT Filed: Oct. 8, 2019

(86) PCT No.: PCT/IB2019/058535
§ 371 (c)(1),
(2) Date: Mar. 30, 2021

(87) PCT Pub. No.: WO2020/075046
PCT Pub. Date: Apr. 16, 2020

(65) Prior Publication Data
US 2022/0041604 A1     Feb. 10, 2022

(30) Foreign Application Priority Data
Oct. 9, 2018   (WO) ................ PCT/CN2018/109415

(51) Int. Cl.
*C07D 487/04*    (2006.01)
*A61K 31/519*    (2006.01)
(Continued)

(52) U.S. Cl.
CPC .......... *C07D 487/04* (2013.01); *A61K 31/519* (2013.01); *A61K 45/06* (2013.01);
(Continued)

(58) Field of Classification Search
CPC ....... A61K 31/519; A61K 45/06; A61P 33/02; C07B 2200/13; C07C 57/15; C07D 487/04
See application file for complete search history.

(56) References Cited

FOREIGN PATENT DOCUMENTS

| WO | 0151919 A2 | 7/2001 |
|----|------------|--------|
| WO | 2004/078163 A2 | 9/2004 |

(Continued)

OTHER PUBLICATIONS

Balbach, et al., Pharmaceutical evaluation of early development candidates, International Journal of Pharmaceutics, May 4, 2004, 1-12, 275(1-2).

(Continued)

*Primary Examiner* — Kortney L. Klinkel
*Assistant Examiner* — Padmaja S Rao
(74) *Attorney, Agent, or Firm* — Emily T. Wu

(57) ABSTRACT

The application relates to N-(4-fluoro-3-(6-(3-methylpyridin-2-yl)-[1,2,4]triazolo[1,5-a]pyrimidin-2-yl)phenyl)-2,4-dimethyloxazole-5-carboxamide (Compound I) fumaric acid co-crystals and X-ray amorphous complexes of Compound (I) and fumaric acid. The application also provides methods of making the same; pharmaceutical compositions comprising them; and their use in treating, preventing, inhibiting, ameliorating, or eradicating the pathology and/or symptomology of a disease caused by a kinetoplastid parasite, such as leishmaniasis, human African trypanosomiasis and Chagas disease.

(Continued)

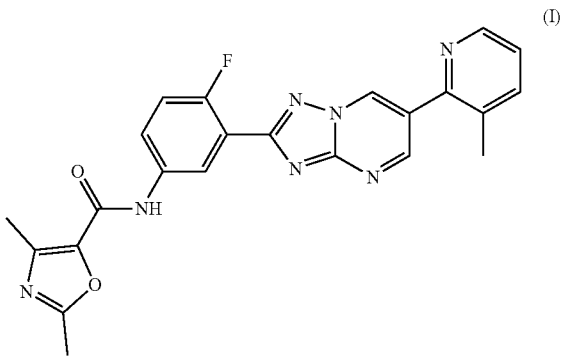

(I)

14 Claims, 18 Drawing Sheets

(51) Int. Cl.
A61K 45/06 (2006.01)
C07C 57/15 (2006.01)
A61P 33/02 (2006.01)

(52) U.S. Cl.
CPC ............ A61P 33/02 (2018.01); C07C 57/15 (2013.01); C07B 2200/13 (2013.01)

(56) References Cited

FOREIGN PATENT DOCUMENTS

WO   2005100364 A1   10/2005
WO   2007/092779 A2   8/2007
WO   2015/095477 A1   6/2015

OTHER PUBLICATIONS

Bastin. et al., Salt Selection and Optimisation Procedures for Pharmaceutical New Chemical Entities, Organic Process Research & Development., 2000, 427-435, 4(5).
Caira, Crystalline Polymorphism of Organic Compounds, Topics in Current Chemistry, 1998, 164-208, 198.
Duggirala et al., Pharmaceutical cocrystals: Along the path to improved medicines, Chem.Commun., 2016, pp. 640-655 (specifically see p. 649: 2nd paragraph from bottom through 6652), 52.
G. A. Kuznetsova, Methodical Instructions, Irkutsk State University (Gouvpoigu), General Physics Department, 2005, p. 3: 2nd paragraph.
J. Bernstein, Polymorphism of Molecular Crystals, New York: Oxford Univ. Press, 2002, pp. 324-330, Chapter 7.3.2: Biodostupnost (Bioavailability).
Klaus Kümmerer, Pharmaceuticals in the environment, Annual Review of Environment and Resources, 2010, pp. 57-75, 35.
M. D. Mashkovsky, Lekarstvennye sredstva (Medicaments: A Guide for Doctors), Manual for physicians, 2005, pp. 10-11, revised, amended, and supplemented, 15th edition.
Morissette et al., High-throughput crystallization: Polymorphs, salts, co-crystals and solvates of pharmaceutical solids, Advanced Drug Delivery Reviews, 2004, pp. 275-300, 56.
Rodriguez-Spong et al., General principles of pharmaceutical solid polymorphism: a supramolecular perspective, Advanced Drug Delivery Reviews, 2004, pp. 241-274, 56.
Singhal, et al., Drug polymorphism and dosage form design: a practical perspective, Advanced Drug Delivery Reviews, Feb. 23, 2004, 335-347, 56(3).
Yadav et al., "Co-Crystals: A Novel Approach to Modify Physicochemical Properties of Active Pharmaceutical Ingredients", Indian Journal of Pharmaceutical Sciences, Jul.-Aug. 2009, pp. 359-370, XP055398519, DOI: 10.4103/0250-474X.57283.
Thakuria et al., "Pharmaceutical cocrystals and poorly soluble drugs", International Journal of Pharmaceutics, 2012, pp. 1-24, XP055067380, ISSN: 0378-5173, DOI: 10.1016/j.ijpharm.2012.10.043.
Pharmaceutical and Food Safety Bureau, Notification No. 568, May 1, 2001, On Establishing Specifications and Test Methods for New Drugs.
Kawaguchi, et al., Drug and crystal polymorphism, Journal of Human Environmental Engineering, 2002, 310-317, 4(2).
Takada, API form screening and selection in drug discovery stage, Pharm Stage, 2007, 20-25, 6(10).
Yamano, Approach to Crystal Polymorph in Process Research of New Drug, Journal of Synthetic Organic Chemistry, 2007, 907-913, 65.
Braga, et al., Crystal Polymorphism and Multiple Crystal Forms, Feb. 25, 2009, 132, 25-50.
Hilfiker, et al., Relevance of Solid-state Properties for Pharmaceutical Products, 2006, chapter 1, 1-19.

SOLID FORMS OF N-(4-FLUORO-3-(6-(3-METHYLPYRIDIN-2-YL)-[1,2,4]TRIAZOLO[1,5-A]PYRIMIDIN-2-YL)PHENYL)-2,4-DIMETHYLOXAZOLE-5-CARBOXAMIDE

CROSS-REFERENCE TO RELATED APPLICATIONS

This application is a 371 U.S. national phase application of international application number PCT/IB2019/058535 filed 8 Oct. 2019, which claims the benefit of PCT/CN2018/109415 filed 9 Oct. 2018; each of which is incorporated by reference herein in its entirety.

FIELD OF THE INVENTION

The present invention is directed to N-(4-fluoro-3-(6-(3-methylpyridin-2-yl)-[1,2,4]triazolo[1,5-a]pyrimidin-2-yl)phenyl)-2,4-dimethyloxazole-5-carboxamide solid forms and methods of making the same; pharmaceutical compositions comprising thereof; and methods of treatment using the same.

BACKGROUND OF THE INVENTION

N-(4-fluoro-3-(6-(3-methylpyridin-2-yl)-[1,2,4]triazolo[1,5-a]pyrimidin-2-yl)phenyl)-2,4-dimethyloxazole-5-carboxamide (Compound I) is a selective inhibitor of the kinetoplastid proteasome, with activity against leishmaniasis, Chagas disease and sleeping sickness. The diseases, caused by infection with the kinetoplastid parasites *Leishmania* spp., *Trypanosoma cruzi* and *Trypanosoma brucei* spp. respectively, affect 20 million people worldwide and lead to more than 50,000 deaths annually. (Khare et al., Nature (2016) 537:229-233).

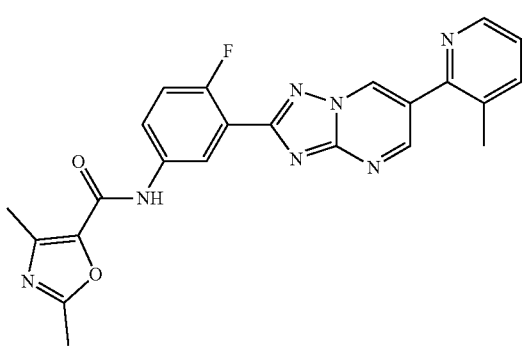

(Compound I)

Compound I is described in WO 2015/095477 as the free form compound.

SUMMARY OF THE INVENTION

The invention provides N-(4-fluoro-3-(6-(3-methylpyridin-2-yl)-[1,2,4]triazolo[1,5-a]pyrimidin-2-yl)phenyl)-2,4-dimethyloxazole-5-carboxamide solid forms.

Various enumerated embodiments of the invention are described herein. Features specified in each embodiment may be combined with other specified features to provide further embodiments of the present invention.

Embodiment 1. A co-crystal comprising N-(4-fluoro-3-(6-(3-methylpyridin-2-yl)-[1,2,4]triazolo[1,5-a]pyrimidin-2-yl)phenyl)-2,4-dimethyloxazole-5-carboxamide and an aliphatic $C_{2-8}$ di-carboxylic acid.

Embodiment 2A. The co-crystal of Embodiment 1, wherein said $C_2$-8 di-carboxylic acid is a $C_4$ di-carboxylic acid. In one embodiment, the $C_4$ di-carboxylic acid is fumaric acid, succinic acid, tartaric acid or maleic acid.

Embodiment 2B. The co-crystal of Embodiment 1, comprising N-(4-fluoro-3-(6-(3-methylpyridin-2-yl)-[1,2,4]triazolo[1,5-a]pyrimidin-2-yl)phenyl)-2,4-dimethyloxazole-5-carboxamide and fumaric acid.

Embodiment 3A. The co-crystal of Embodiment 2B, wherein the molar ratio of N-(4-fluoro-3-(6-(3-methylpyridin-2-yl)-[1,2,4]triazolo[1,5-a]pyrimidin-2-yl)phenyl)-2,4-dimethyloxazole-5-carboxamide to fumaric acid is 2:(0.5-2.5). In one embodiment, the molar ratio of N-(4-fluoro-3-(6-(3-methylpyridin-2-yl)-[1,2,4]triazolo[1,5-a]pyrimidin-2-yl)phenyl)-2,4-dimethyloxazole-5-carboxamide to fumaric acid is 2:(0.8-1.2) or 1:(0.8-1.2).

Embodiment 3C. The co-crystal of Embodiment 2B, wherein the molar ratio of N-(4-fluoro-3-(6-(3-methylpyridin-2-yl)-[1,2,4]triazolo[1,5-a]pyrimidin-2-yl)phenyl)-2,4-dimethyloxazole-5-carboxamide to fumaric acid is about 1:1; for example, 1:(0.7-1.3); preferably 1:(0.8-1.2), and more preferably 1:(0.9-1.1). In one embodiment, the molar ratio of N-(4-fluoro-3-(6-(3-methylpyridin-2-yl)-[1,2,4]triazolo[1,5-a]pyrimidin-2-yl)phenyl)-2,4-dimethyloxazole-5-carboxamide to fumaric acid is 1:(0.8-1.2). In another embodiment, the molar ratio of N-(4-fluoro-3-(6-(3-methylpyridin-2-yl)-[1,2,4]triazolo[1,5-a]pyrimidin-2-yl)phenyl)-2,4-dimethyloxazole-5-carboxamide to fumaric acid is 1:1.

Embodiment 3D. The co-crystal of Embodiment 2B, wherein the molar ratio of N-(4-fluoro-3-(6-(3-methylpyridin-2-yl)-[1,2,4]triazolo[1,5-a]pyrimidin-2-yl)phenyl)-2,4-dimethyloxazole-5-carboxamide to fumaric acid is about 2:1; for example, 2:(0.7-1.3); preferably 2:(0.8-1.2), and more preferably 2:(0.9-1.1). In one embodiment, the molar ratio of N-(4-fluoro-3-(6-(3-methylpyridin-2-yl)-[1,2,4]triazolo[1,5-a]pyrimidin-2-yl)phenyl)-2,4-dimethyloxazole-5-carboxamide to fumaric acid is 2:(0.8-1.2). In another embodiment, the molar ratio of N-(4-fluoro-3-(6-(3-methylpyridin-2-yl)-[1,2,4]triazolo[1,5-a]pyrimidin-2-yl)phenyl)-2,4-dimethyloxazole-5-carboxamide to fumaric acid is 2:1.

Embodiment 4. The co-crystal of Embodiment 2B, having an X-ray powder diffraction pattern comprising three or more 2θ peaks selected from about 9.4°, 11.0°, 14.2° and 25.8° (2θ); preferably at 9.4°±0.2°, 11.00° 0.2°, 14.2°±0.2° and 25.8°±0.2° (2θ); when measured with a CuKα radiation at a wavelength of 0.15 nm at room temperature.

Embodiment 5. The co-crystal of Embodiment 2B, having an X-ray powder diffraction pattern comprising 2θ peaks at about 9.4°, 14.2° and 25.8° (2θ); preferably at 9.4°±0.2°, 14.2°±0.2° and 25.8°±0.2° (2θ); when measured with a CuKα radiation at a wavelength of 0.15 nm at room temperature.

Embodiment 6. The co-crystal of Embodiment 2B, which is characterized by one of more selected from: (a) an X-ray powder diffraction pattern that is substantially as shown in FIG. 1 when measured with a CuKα radiation at a wavelength of 0.15 nm at room temperature; (b) a differential scanning calorimetry (DSC) thermogram that is substantially as shown in FIG. 2, and optionally having a DSC thermogram comprising an endothermic peak at about 225.4° C., preferably 225.4° C.±2° C., all when heated from 30 to 300° C. at a rate of 10 K/min; and (c) a thermogravimetric analysis (TGA) diagram that is substantially as shown in FIG. 3 when heated from 30 to 300° C. at a rate of 10 K/min.

Embodiment 7. The co-crystal of Embodiment 2B, having an X-ray powder diffraction pattern comprising three or more 2θ peaks selected from about 13.4°, 15.7°, 23.9° and 24.7° (2θ); preferably at 13.4°±0.2°, 15.7°±0.2°, 23.9°±0.2° and 24.7°±0.2° (2θ); when measured with a CuKα radiation at a wavelength of 0.15 nm at room temperature.

Embodiment 8. The co-crystal of Embodiment 2B, having an X-ray powder diffraction pattern comprising 2θ peaks at about 15.7°, 23.9° and 24.7° (2θ); preferably at 15.7°±0.20, 23.9°±0.2° and 24.7°±0.2° (2θ); when measured with a CuKα radiation at a wavelength of 0.15 nm at room temperature.

Embodiment 9. The co-crystal of Embodiment 2B, which is characterized by one of more selected from: (a) an X-ray powder diffraction pattern that is substantially as shown in FIG. 4 when measured with a CuKα radiation at a wavelength of 0.15 nm at room temperature; (b) a differential scanning calorimetry (DSC) thermogram that is substantially as shown in FIG. 5, and optionally having a DSC thermogram comprising an endothermic peak at about 227.3° C., preferably at 227.3° C.±2° C., all when heated from 30 to 300° C. at a rate of 10 K/min; and (c) a thermogravimetric analysis (TGA) diagram that is substantially as shown in FIG. 6 when heated from 30 to 300° C. at a rate of 10 K/min.

Embodiment 10. The co-crystal of Embodiment 2B, having an X-ray powder diffraction pattern comprising three or more 2θ peaks selected from about 9.8°, 11.3°, 14.8°, 24.6°, 25.0°, 26.5° and 27.6° (2θ); preferably at 9.8°±0.2°, 11.3°±0.2°, 14.8°±0.2°, 24.6°±0.2°, 25.0°±0.2°, 26.5°±0.2° and 27.6°±0.2° (2θ); when measured with a CuKα radiation at a wavelength of 0.15 nm at room temperature.

Embodiment 11. The co-crystal of Embodiment 2B, having an X-ray powder diffraction pattern comprising 2θ peaks at about 9.8°, 14.8° and 27.6° (2θ); preferably at 9.8°±0.2°, 14.8°±0.2° and 27.6°±0.2° (2θ); when measured with a CuKα radiation at a wavelength of 0.15 nm at room temperature.

Embodiment 12. The co-crystal of Embodiment 2B, which is characterized by one of more selected from: (a) an X-ray powder diffraction pattern that is substantially as shown in FIG. 7 when measured with a CuKα radiation at a wavelength of 0.15 nm at room temperature; (b) a differential scanning calorimetry (DSC) thermogram that is substantially as shown in FIG. 8, and optionally having a DSC thermogram comprising an endothermic peak at about 224.7° C., preferably at 224.7° C.±2° C., all when heated from 30 to 300° C. at a rate of 10 K/min; and (c) a thermogravimetric analysis (TGA) diagram that is substantially as shown in FIG. 9 when heated from 30 to 300° C. at a rate of 10 K/min.

Embodiment 13. The co-crystal of Embodiment 2B, having an X-ray powder diffraction pattern comprising three or more 2θ peaks selected from about 3.8°, 13.5°, 17.2° and 26.6° (2θ); preferably at 3.8°±0.2°, 13.5°±0.2°, 17.2°±0.2° and 26.6°±0.2° (2θ); when measured with a CuKα radiation at a wavelength of 0.15 nm at room temperature.

Embodiment 14. The co-crystal of Embodiment 2B, having an X-ray powder diffraction pattern comprising 2θ peaks at about 3.8°, 13.5° and 17.2° (2θ); preferably at 3.8° 0.2°, 13.5°±0.2° and 17.2°±0.2° (2θ); when measured with a CuKα radiation at a wavelength of 0.15 nm at room temperature.

Embodiment 15. The co-crystal of Embodiment 2B, which is characterized by one of more selected from: (a) an X-ray powder diffraction pattern that is substantially as shown in FIG. 10 when measured with a CuKα radiation at a wavelength of 0.15 nm at room temperature; (b) a differential scanning calorimetry (DSC) thermogram that is substantially as shown in FIG. 11, and optionally having a DSC thermogram comprising an endothermic peak at about 206.4° C., preferably at 206.4° C.±2° C., when heated from 30 to 300° C. at a rate of 10 K/min; and (c) a thermogravimetric analysis (TGA) diagram that is substantially as shown in FIG. 12 when heated from 30 to 300° C. at a rate of 10 K/min.

Embodiment 16. The co-crystal according to any one of Embodiments 1, 2A, 2B, 3A-3D, and 4-15, in a substantially pure form.

Embodiment 17. A composition comprising a co-crystal according to any one of the above Embodiments.

Embodiment 18. The composition according to Embodiment 17, comprising at least 90% by weight of said co-crystal based on the weight of the composition.

Embodiment 19. A composition consisting essentially of the co-crystal according to any one of Embodiments 1, 2A, 2B, 3A-3D, and 4-16.

Embodiment 20. A pharmaceutical composition comprising the co-crystal according to any one of Embodiments 1, 2A, 2B, 3A-3D, and 4-16, and a pharmaceutically acceptable carrier.

Embodiment 21. A combination comprising the co-crystal according to any one of Embodiments 1, 2A, 2B, 3A-3D and 4-16, and one or more therapeutically active agent(s).

Embodiment 22. A co-crystal according to any one of Embodiments 1, 2A, 2B, 3A-3D and 4-16, and optionally in combination with a second agent, for treating a disorder or disease selected from leishmaniasis, Chagas diseases and human African trypanosomiasis.

Embodiment 23. Use of a co-crystal according to any one of Embodiments 1, 2A, 2B, 3A-3D and 4-16, and optionally in combination with a second agent, for treating leishmaniasis, Chagas diseases or human African trypanosomiasis.

Embodiment 23A. Use of a co-crystal according to any one of Embodiments 1, 2A, 2B, 3A-3D and 4-16, and optionally in combination with a second agent, in the manufacture of a medicament for the treatment of a disorder or disease selected from leishmaniasis, Chagas diseases and human African trypanosomiasis.

Embodiment 24. The co-crystal for treating a disorder or disease according to Embodiment 22, or the use according to Embodiments 23 or 23A; wherein said second agent is selected from: (a) stibogluconate, meglumine antimoniate, amphotericin, miltefosine, and paromomycin or a combination thereof, for the treatment of visceral leishmaniasis or cutaneous leishmaniasis; (b) benznidazole, nifurtimox and amphotericin or a combination thereof, for the treatment of Chagas disease; and (c) pentamidine, suramin, melarsoprol, eflornithine, and nifurtimox or a combination thereof, for the treatment of human African trypanosomiasis.

Embodiment 25A. The co-crystal for treating a disorder or disease according to Embodiment 24, or the use according to Embodiment 24; wherein said disease is visceral leishmaniasis or cutaneous leishmaniasis.

Embodiment 25B. The co-crystal for treating a disorder or disease according to Embodiment 25A, or the use according to Embodiment 25A; wherein said second agent is selected from stibogluconate, meglumine antimoniate, amphotericin, miltefosine, and paromomycin, or a combination thereof.

Embodiment 25C. The co-crystal for treating a disorder or disease according to Embodiment 24, or the use according to Embodiment 24; wherein said disease is Chagas disease.

Embodiment 25D. The co-crystal for treating a disorder or disease according to Embodiment 25C, or the use according to Embodiment 25C; wherein said second agent is selected from benznidazole, nifurtimox and amphotericin, or a combination thereof.

Embodiment 25E. The co-crystal for treating a disorder or disease according to Embodiment 24, or the use according to Embodiment 24; wherein said disease is human African trypanosomiasis.

Embodiment 25F. The co-crystal for treating a disorder or disease according to Embodiment 25E, or the use according to Embodiment 25E; wherein said second agent is pentamidine, suramin, melarsoprol, eflornithine, and nifurtimox, or a combination thereof.

Embodiment 26. A method for treating, preventing, inhibiting, ameliorating, or eradicating the pathology and/or symptomology of a disease caused by a parasite, comprising administering to a subject a therapeutically effective amount of a pharmaceutical composition comprising a co-crystal according to any one of Embodiments 1, 2A, 2B, 3A-3D and 4-16, at least one pharmaceutically acceptable carrier, and optionally in combination with a second agent, wherein the disease is selected from leishmaniasis, human African trypanosomiasis and Chagas disease.

Embodiment 27. The method according to Embodiment 26, wherein said pharmaceutical composition is to be administered at a dose in a range of about 10 mg to about 500 mg.

Embodiment 28. The method according to Embodiment 26, wherein said pharmaceutical composition is to be administered at a dose in a range of about 10 mg to about 400 mg.

Embodiment 29. The method according to Embodiment 26, wherein said pharmaceutical composition is to be administered at a dose in a range of about 50 mg to about 250 mg.

Embodiment 30. The method according to Embodiment 26, wherein said pharmaceutical composition is to be administered at a dose in a range of about 50 mg to about 150 mg.

Embodiment 31. The method according to Embodiment 26, wherein said pharmaceutical composition is to be administered at a dose in a range of about 100 mg to about 150 mg.

Embodiment 32. The method according to any one of Embodiments 26-31, wherein said pharmaceutical composition is to be administered once or twice daily.

Embodiment 33. The method according to any one of Embodiments 26-32, wherein said pharmaceutical composition is to be administered orally.

Embodiment 34. A kit comprising (i) a pharmaceutical composition comprising a co-crystal according to any one of Embodiments 1, 2A, 2B, 3A-3D and 4-16, at least one pharmaceutically acceptable carrier, and optionally in combination with a second agent; and (ii) instructions for administration.

Embodiment 35. A process for preparing a co-crystal according to any one of Embodiments 1, 2A, 2B, 3A-3D and 4-16, comprising contacting (1) fumaric acid optionally in a first solvent, with (2) N-(4-fluoro-3-(6-(3-methylpyridin-2-yl)-[1,2,4]triazolo[1,5-a]pyrimidin-2-yl)phenyl)-2,4-dimethyloxazole-5-carboxamide optionally in a second solvent, under suitable conditions to form N-(4-fluoro-3-(6-(3-methylpyridin-2-yl)-[1,2,4]triazolo[1,5-a]pyrimidin-2-yl)phenyl)-2,4-dimethyloxazole-5-carboxamide fumaric acid co-crystals.

Embodiment 36. The process according to Embodiment 35, comprising (1) adding fumaric acid to a first solvent to form a fumaric acid solution; (2) adding N-(4-fluoro-3-(6-(3-methylpyridin-2-yl)-[1,2,4]triazolo[1,5-a]pyrimidin-2-yl)phenyl)-2,4-dimethyloxazole-5-carboxamide to a second solvent to form a N-(4-fluoro-3-(6-(3-methylpyridin-2-yl)-[1,2,4]triazolo[1,5-a]pyrimidin-2-yl)phenyl)-2,4-dimethyloxazole-5-carboxamide solution; and (3) contacting said fumaric acid solution with said N-(4-fluoro-3-(6-(3-methylpyridin-2-yl)-[1,2,4]triazolo[1,5-a]pyrimidin-2-yl)phenyl)-2,4-dimethyloxazole-5-carboxamide solution under suitable conditions, optionally heating the reaction mixture between 40-70° C., between 40-60° C. or between 45-55° C., to form a N-(4-fluoro-3-(6-(3-methylpyridin-2-yl)-[1,2,4]triazolo[1,5-a]pyrimidin-2-yl)phenyl)-2,4-dimethyloxazole-5-carboxamide fumaric acid co-crystals.

Embodiment 37. The process according to Embodiment 36, comprising adding said N-(4-fluoro-3-(6-(3-methylpyridin-2-yl)-[1,2,4]triazolo[1,5-a]pyrimidin-2-yl)phenyl)-2,4-dimethyloxazole-5-carboxamide solution to said fumaric acid solution under suitable conditions, optionally heating the reaction mixture between 45-55° C., to form said N-(4-fluoro-3-(6-(3-methylpyridin-2-yl)-[1,2,4]triazolo[1,5-a]pyrimidin-2-yl)phenyl)-2,4-dimethyloxazole-5-carboxamide fumaric acid co-crystal. In one embodiment, the molar ratio of N-(4-fluoro-3-(6-(3-methylpyridin-2-yl)-[1,2,4]triazolo[1,5-a]pyrimidin-2-yl)phenyl)-2,4-dimethyloxazole-5-carboxamide to fumaric acid is about 1:1 ("Compound I fumaric acid co-crystal (1:1)").

Embodiment 38. The process according to Embodiment 36, comprising adding said fumaric acid solution to said N-(4-fluoro-3-(6-(3-methylpyridin-2-yl)-[1,2,4]triazolo[1,5-a]pyrimidin-2-yl)phenyl)-2,4-dimethyloxazole-5-carboxamide solution under suitable conditions, optionally heating the reaction mixture between 45-55° C., to form said N-(4-fluoro-3-(6-(3-methylpyridin-2-yl)-[1,2,4]triazolo[1,5-a]pyrimidin-2-yl)phenyl)-2,4-dimethyloxazole-5-carboxamide fumaric acid co-crystal. In one embodiment, the molar ratio of N-(4-fluoro-3-(6-(3-methylpyridin-2-yl)-[1,2,4]triazolo[1,5-a]pyrimidin-2-yl)phenyl)-2,4-dimethyloxazole-5-carboxamide to fumaric acid is about 2:1 ("Compound I fumaric acid co-crystal (2:1)").

Embodiment 39. The process according to any one of claims 35-38, wherein said first solvent is isopropyl alcohol.

Embodiment 40. The process according to any one of claims 35-38, wherein said second solvent is tetrahydrofuran.

Embodiment 41. An X-ray amorphous complex of N-(4-fluoro-3-(6-(3-methylpyridin-2-yl)-[1,2,4]triazolo[1,5-a]pyrimidin-2-yl)phenyl)-2,4-dimethyloxazole-5-carboxamide and fumaric acid; wherein the molar ratio of N-(4-fluoro-3-(6-(3-methylpyridin-2-yl)-[1,2,4]triazolo[1,5-a]pyrimidin-2-yl)phenyl)-2,4-dimethyloxazole-5-carboxamide and fumaric acid is 2:(0.1-5); and optionally substantially free of crystalline forms.

Embodiment 42. The X-ray amorphous complex of Embodiment 41, wherein the molar ratio of N-(4-fluoro-3-(6-(3-methylpyridin-2-yl)-[1,2,4]triazolo[1,5-a]pyrimidin-2-yl)phenyl)-2,4-dimethyloxazole-5-carboxamide and fumaric acid is 1:(0.5-2.5); 1:(0.8-2.3), 1:(0.7-1.3), 1:(0.8-1.2), 1:(0.9-1.1), 1:1; 2:(0.1-1.2), 2:(0.5-1.1), 2:(0.1-0.5), 2:(0.7-1.3), 2:(0.8-1.2), 2:(0.9-1.1) or 2:1.

Embodiment 43. The X-ray amorphous complex according to Embodiment 41, wherein the molar ratio of N-(4-fluoro-3-(6-(3-methylpyridin-2-yl)-[1,2,4]triazolo[1,5-a]pyrimidin-2-yl)phenyl)-2,4-dimethyloxazole-5-carboxamide and fumaric acid is 1:(0.5-2.5), preferably 1:(0.8-2.3).

Embodiment 44. The X-ray amorphous complex according to Embodiment 41, wherein the molar ratio of N-(4-fluoro-3-(6-(3-methylpyridin-2-yl)-[1,2,4]triazolo[1,5-a]pyrimidin-2-yl)phenyl)-2,4-dimethyloxazole-5-carboxamide and fumaric acid is 1:(0.7-1.3), preferably 1:(0.8-1.2) and more preferably 1:(0.9-1.1). In one embodiment, the molar ratio of N-(4-fluoro-3-(6-(3-methylpyridin-2-yl)-[1,2,4]triazolo[1,5-a]pyrimidin-2-yl)phenyl)-2,4-dimethyloxazole-5-carboxamide to fumaric acid is 1:1.

Embodiment 45. The X-ray amorphous complex according to Embodiment 41, wherein the molar ratio of N-(4-fluoro-3-(6-(3-methylpyridin-2-yl)-[1,2,4]triazolo[1,5-a]pyrimidin-2-yl)phenyl)-2,4-dimethyloxazole-5-carboxamide and fumaric acid is 2:(0.1-1.2), preferably 2:(0.5-1.1) or 2:(0.1-0.5).

Embodiment 46. The X-ray amorphous complex according to Embodiment 41, wherein the molar ratio of N-(4-fluoro-3-(6-(3-methylpyridin-2-yl)-[1,2,4]triazolo[1,5-a]pyrimidin-2-yl)phenyl)-2,4-dimethyloxazole-5-carboxamide and fumaric acid is 2:(0.7-1.3), preferably 2:(0.8-1.2) and more preferably 2:(0.9-1.1). In one embodiment, the molar ratio of N-(4-fluoro-3-(6-(3-methylpyridin-2-yl)-[1,2,4]triazolo[1,5-a]pyrimidin-2-yl)phenyl)-2,4-dimethyloxazole-5-carboxamide to fumaric acid is 2:1.

DETAILED DESCRIPTION OF THE INVENTION

Figure 1:
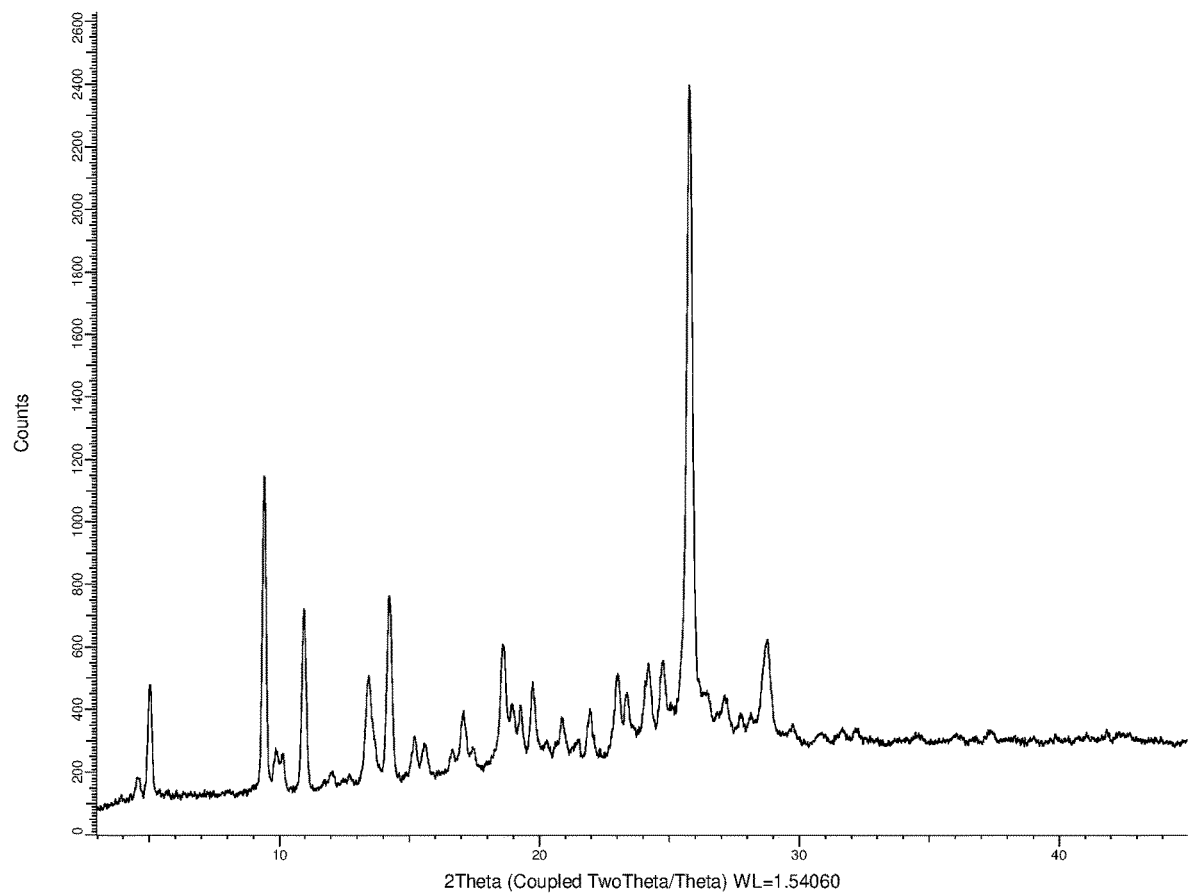
FIG. 1 shows an XRPD pattern of Compound I fumaric acid co-crystal (1:1) Form A.

In one aspect, the invention provides N-(4-fluoro-3-(6-(3-methylpyridin-2-yl)-[1,2,4]triazolo[1,5-a]pyrimidin-2-yl)phenyl)-2,4-dimethyloxazole-5-carboxamide (Compound I) fumaric acid co-crystals, and methods of making the same; pharmaceutical compositions comprising thereof, and methods of treatment using such compositions. The co-crystals of the present invention possess one or more improved physicochemical properties selected from dissolution rate, solubility, chemical stability, physical stability, hygroscopicity, melting point, morphology, flowability, bulk density, and compressibility, as compared to the free form. As a result, a pharmaceutical composition comprising at least one co-crystal of the present invention may have improved pharmacokinetic and/or pharmacodynamic effects in animals, such as humans, as compared to a pharmaceutical composition comprising the free form. As another result, a pharmaceutical composition comprising at least one co-crystal of the present invention may possess one or more improved drug product attributes selected from oral dosage form size, compatibility with one or more desirable pharmaceutically acceptable carriers, storage life, and storage conditions, as compared to the free form.

In another aspect, the invention provides an X-ray amorphous complex of N-(4-fluoro-3-(6-(3-methylpyridin-2-yl)-[1,2,4]triazolo[1,5-a]pyrimidin-2-yl)phenyl)-2,4-dimethyloxazole-5-carboxamide and fumaric acid; wherein the molar ratio of N-(4-fluoro-3-(6-(3-methylpyridin-2-yl)-[1,2,4]triazolo[1,5-a]pyrimidin-2-yl)phenyl)-2,4-dimethyloxazole-5-carboxamide and fumaric acid is about 1:1 or 2:1; and optionally substantially free of crystalline forms.

Definitions

As used herein, the term "co-crystal(s)" refers to single phase crystalline materials comprising two or more components in a specific stoichiometric ratio, where the arrangement in the crystal lattice is not based on ionic bonds (as with salts) and at least two of the components are solids at room temperature.

As used herein, the term "aliphatic $C_{2-8}$ dicarboxylic acid" refers to a straight-chained or branched, saturated or unsaturated, substituted or unsubstituted dicarboxylic acid having from 2-8 carbon atoms, preferably from 4-6 carbon atoms, including but not limited to fumaric acid, succinic acid, maleic acid, and tartaric acid.

As used herein, the term "Compound I fumaric acid co-crystal (1:1)" refer to N-(4-fluoro-3-(6-(3-methylpyridin-2-yl)-[1,2,4]triazolo[1,5-a]pyrimidin-2-yl)phenyl)-2,4-dimethyloxazole-5-carboxamide (Compound I) fumaric acid co-crystals having a Compound I: fumaric acid stoichiometric ratio of about 1:1; for example, 1:(0.7-1.3), 1:(0.8-1.2) or 1:(0.9-1.1) or 1:1.

As used herein, the term "Compound I fumaric acid co-crystal (2:1)" refer to N-(4-fluoro-3-(6-(3-methylpyridin-2-yl)-[1,2,4]triazolo[1,5-a]pyrimidin-2-yl)phenyl)-2,4-dimethyloxazole-5-carboxamide (Compound I) fumaric acid co-crystals having a Compound I: fumaric acid stoichiometric ratio of about 2:1; for example, 2:(0.7-1.3), 2:(0.8-1.2), 2:(0.9-1.1) or 2:1.

As used herein, the terms "Form A", "Form B", "Form C", etc. used to characterize specific co-crystal embodiments are mere identifiers that should be interpreted according to the characterization information presented herein; and should not be considered limiting with respect to any other substance possessing similar or identical physical and chemical characteristics.

As used herein, the term "amorphous" refers to a solid form of a molecule, atom, and/or ion that is not crystalline. An amorphous solid does not display a definitive X-ray diffraction pattern.

As used herein, the term "amorphous Compound I fumaric acid (1:1)" refer to an X-ray amorphous complex of N-(4-fluoro-3-(6-(3-methylpyridin-2-yl)-[1,2,4]triazolo[1,5-a]pyrimidin-2-yl)phenyl)-2,4-dimethyloxazole-5-carboxamide (Compound I) and fumaric acid having a Compound I: fumaric acid stoichiometric ratio of about 1:1, for example, 1:(0.7-1.3), 1:(0.8-1.2), 1:(0.9-1.1) or 1:1; and wherein the complex may comprise co-crystal, salt and solid dispersion forms.

As used herein, the term "amorphous Compound I fumaric acid (2:1)" refer to an X-ray amorphous complex of N-(4-fluoro-3-(6-(3-methylpyridin-2-yl)-[1,2,4]triazolo[1,5-a]pyrimidin-2-yl)phenyl)-2,4-dimethyloxazole-5-carboxamide (Compound I) and fumaric acid having a Compound I: fumaric acid stoichiometric ratio of about 2:1, for example, 2:(0.7-1.3), 2:(0.8-1.2), 2:(0.9-1.1) or 2:1; and wherein the complex may comprise co-crystal, salt and solid dispersion forms.

As used herein, the term "substantially pure" in reference to the co-crystals of the invention, means a co-crystal form having a purity greater than 80 weight %, including greater than 85, 90, 95, 96, 97, 98, and 99 weight %, and also including equal to about 100 weight % of co-crystal, based on the weight of the composition. The remaining material comprises other co-crystalline form(s), reaction impurities, and/or processing impurities arising from its preparation.

For example, a co-crystalline Form A may be deemed substantially pure in that it has a purity greater than 90 weight %, as measured by means known and generally accepted in the art, where the remaining less than 10 weight % of material comprises other co-crystalline form(s), reaction impurities, and/or processing impurities. The presence of reaction impurities and/or processing impurities may be determined by analytical techniques known in the art, such as, for example, chromatography, nuclear magnetic resonance spectroscopy, mass spectrometry, or infrared spectroscopy.

As used herein, the term "room temperature" (RT) refers to a temperature in the range of from 20° C. to 30° C. as measured under standard conditions. Typically, standard conditions can additionally mean a measurement under 20-50% relative humidity. In one embodiment, "room temperature" refers to a temperature of about 22° C.-25° C.

As used herein, the term "about" means within a statistically meaningful range of a value. Such a range can be within an order of magnitude, typically within 10%, more typically within 5%, even more typically within 1%, and most typically within 0.1% of the indicated value or range. Sometimes, such a range can lie within experimental error, typical of standard methods used for the measurement and/or determination of a given value or range.

As used herein, the term "endothermic peak" refers to the melting peak in a differential scanning calorimetry (DSC) thermogram.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, $22^{nd}$ Ed. Pharmaceutical Press, 2013, pp. 1049-1070).

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder.

As used herein, the term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In a non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease caused by the proliferation of a kinetoplastid parasite; or (2) reduce or inhibit the proliferation of a kinetoplastid parasite.

As used herein, the term "subject" refers to primates (e.g., humans (male or female), dogs, rabbits, guinea pigs, pigs, rats and mice). In certain embodiments, the subject is a primate. In yet other embodiments, the subject is a human.

As used herein, the term "a," "an," "the" and similar terms used in the context of the present invention (especially in the context of the claims) are to be construed to cover both the singular and plural unless otherwise indicated herein or clearly contradicted by the context.

Aspects of the Invention

In one aspect, the invention provides Compound I fumaric acid co-crystals. In one embodiment, the invention provides Compound I fumaric acid co-crystal (1:1) Form A, Form B or Form C; or Compound I fumaric acid co-crystals (2:1). In another embodiment, the invention provides substantially pure Compound I fumaric acid co-crystal (1:1) Form A, Form B or Form C; or substantially pure Compound I fumaric acid co-crystal (2:1). In yet another embodiment, the invention provides a composition consisting essentially of Compound I fumaric acid co-crystal (1:1) Form A, Form B or Form C; or a composition consisting essentially of Compound I fumaric acid co-crystal (2:1).

The co-crystals of the invention may be characterized as having an X-ray powder diffraction pattern, differential scanning calorimetry (DSC) thermogram, or thermogravimetric analysis (TGA) diagram that is "substantially as shown in" a figure (e.g., FIG. 1). One skilled in the art will understand that certain variabilities in peak positions and relative intensities may occur due to inter-apparatus and sample variability (e.g., concentration, purity, degree of crystallinity, orientation, preparation, etc.) and other factors known to those skilled in the art, but still relate to the same solid form. One skilled in the art will also appreciate that variabilities in relative peak intensities can occur within acceptable experimental error. For example, diffraction angles (2θ) in an XRPD pattern are collected with a variance of about ±0.3° (2θ), preferably about ±0.2° (2θ), more preferably at about ±0.1° (2θ), and even more preferably at ±0.05° (2θ). TGA determinations are collected with a variance of about ±0.3%, preferably about 0.2%, more preferably at about ±0.1%. Melting point determinations based on DSC have a variability of ±3° C., preferably ±2° C., more preferably ±1° C.

Preferably, the crystalline form has substantially pure phase homogeneity as indicated by less than 10%, preferably less than 5%, and more preferably less than 2% of the total peak area in the experimentally measured XRPD pattern arising from the extra peaks that are absent from the simulated XRPD pattern. Most preferred is a crystalline form having substantially pure phase homogeneity with less than 1% of the total peak area in the experimentally measured XRPD pattern arising from the extra peaks that are absent from the simulated XRPD pattern.

In another aspect, the invention provides X-ray amorphous complexes of Compound I and fumaric acid; wherein the molar ratio of Compound I is about 1:1 or 2:1; and optionally, substantially free of crystalline forms. In one embodiment, the invention provides substantially pure X-ray amorphous complexes of Compound I and fumaric acid as described herein. In yet another embodiment, the invention provides a composition consisting essentially of an X-ray amorphous complex of Compound I and fumaric acid, wherein the molar ratio of Compound I and fumaric acid is about 1:1 or 2:1.

Pharmaceutical Compositions, Dosage and Administration

In yet another aspect, the invention provides a pharmaceutical composition comprising Compound I fumaric acid co-crystals and/or amorphous Compound I fumaric acid, and a pharmaceutically acceptable carrier.

In one embodiment, the invention provides a pharmaceutical composition comprising at least one of Compound I fumaric acid co-crystals (1:1) Form A, Form B or Form C, Compound I fumaric acid co-crystal (2:1), amorphous Compound 1 fumaric acid (1:1), or amorphous Compound I fumaric acid (2:1); and a pharmaceutically acceptable carrier. The pharmaceutically acceptable carrier can readily be selected by one of ordinary skill in the art according to the desired mode of administration. Illustrative examples of suitable modes of administration include oral, nasal, parenteral, topical, transdermal, and rectal.

The compositions of the invention may take any pharmaceutical form recognizable to the skilled artisan as being suitable. Suitable pharmaceutical forms include solid, semi-solid, liquid, or lyophilized formulations, such as tablets, powders, capsules, suppositories, suspensions, liposomes, and aerosols. In one embodiment, the invention provides a pharmaceutical composition comprising Compound I fumaric acid co-crystals (1:1) Form A, Form B or Form C, Compound I fumaric acid co-crystal (2:1), amorphous Compound 1 fumaric acid (1:1), or amorphous Compound I fumaric acid (2:1); for oral or parenteral administration.

The pharmaceutical compositions of the invention can be in unit dosage of about 1-1000 mg of active ingredient for a subject of about 50-70 kg; or about 1-600 mg; or about 1-400 mg; or about 1-300 mg; or about 1-150 mg; or about 1-50 mg of active ingredient. The therapeutically effective dosage of the composition is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compositions of the invention can be applied in vitro in the form of solutions, e.g., aqueous solutions, and in vivo either enterally, parenterally, advantageously intravenously, e.g., as a suspension or in aqueous solution. The dosage in vitro may range between about 10-3 molar and 10-9 molar concentrations.

The invention further provides therapeutic regimens for treating, preventing, inhibiting, ameliorating, or eradicating the pathology and/or symptomology of a disease caused by a kinetoplastid parasite. In one embodiment, the invention provides methods for treating, a disease caused by a kinetoplastid parasite, comprising administering a composition comprising Compound I fumaric acid co-crystals (1:1) Form A, Form B or Form C, Compound I fumaric acid co-crystal (2:1), amorphous Compound 1 fumaric acid (1:1), or amorphous Compound I fumaric acid (2:1); to a subject in need thereof; at a dose in a range of about 10 mg to about 400 mg; about 30 mg to about 300 mg; about 100 mg to about 300 mg; or about 100 mg to about 150 mg. In some embodiments, the composition is administered at a dose of about 10 mg, about 30 mg, about 50 mg, about 100 mg, about 150 mg, about 300 mg, about 400 mg, or about 600 mg. Such doses may be for oral administration; and may be for daily administration (e.g. once or twice daily administration).

The pharmaceutical compositions of the present invention may be administered either simultaneously with, or before or after, one or more other therapeutic agent. The compositions of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

In one embodiment, the invention provides a product comprising Compound I fumaric acid co-crystals (1:1) Form A, Form B or Form C, Compound I fumaric acid co-crystal (2:1), amorphous Compound 1 fumaric acid (1:1), or amorphous Compound I fumaric acid (2:1); and at least one other therapeutic agent as a combined preparation for simultaneous, separate or sequential use in therapy. Products provided as a combined preparation include a composition comprising Compound I fumaric acid co-crystals (1:1) Form A, Form B or Form C, Compound I fumaric acid co-crystal (2:1), amorphous Compound 1 fumaric acid (1:1), or amorphous Compound I fumaric acid (2:1); and the other therapeutic agent(s), together in the same pharmaceutical composition or in separate form, e.g. in the form of a kit. Optionally, the pharmaceutical composition may comprise a pharmaceutically acceptable carrier, as described above.

In one embodiment, the invention provides a kit comprising two or more separate pharmaceutical compositions, at least one of which contains Compound I fumaric acid co-crystals (1:1) Form A, Form B or Form C, Compound I fumaric acid co-crystal (2:1), amorphous Compound 1 fumaric acid (1:1), or amorphous Compound I fumaric acid (2:1). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a composition comprising Compound I fumaric acid co-crystals (1:1) Form A, Form B or Form C, Compound I fumaric acid co-crystal (2:1), amorphous Compound 1 fumaric acid (1:1), or amorphous Compound I fumaric acid (2:1); for treating a disease or condition caused by the growth and proliferation of a kinetoplastid parasite, wherein the medicament is prepared for administration with another therapeutic agent. The invention also provides the use of another therapeutic agent for treating a disease or condition caused by the growth and proliferation of a kinetoplastid parasite, wherein the medicament is administered with Compound I fumaric acid co-crystals (1:1) Form A, Form B or Form C, Compound I fumaric acid co-crystal (2:1), amorphous Compound 1 fumaric acid (1:1), or amorphous Compound I fumaric acid (2:1).

The invention also provides the use of a composition comprising Compound I fumaric acid co-crystals (1:1) Form A, Form B or Form C, Compound I fumaric acid co-crystal (2:1), amorphous Compound 1 fumaric acid (1:1), or amorphous Compound I fumaric acid (2:1); for treating a disease or condition caused by the growth and proliferation of a kinetoplastid parasite, wherein the patient has previously (e.g. within 24 hours) been treated with another therapeutic agent. The invention also provides the use of another therapeutic agent for treating a disease or condition caused by the growth and proliferation of a kinetoplastid parasite, wherein the patient has previously (e.g. within 24 hours) been treated with Compound I fumaric acid co-crystals (1:1) Form A, Form B or Form C, Compound I fumaric acid co-crystal (2:1), amorphous Compound 1 fumaric acid (1:1), or amorphous Compound I fumaric acid (2:1).

In one embodiment, the other therapeutic agent is selected from stibogluconate, meglumine antimoniate, amphotericin, miltefosine and paromomycin or a combination thereof, for the treatment of Leishmaniasis. In another embodiment, the other therapeutic agent is selected from benznidazole, nifurtimox and amphotericin or a combination thereof, for the treatment of Chagas disease. In yet another, the other therapeutic agent is selected from pentamidine, suramin, melarsoprol, eflornithine, and nifurtimox or a combination thereof, for treatment of human African trypanosomiasis. Where the pharmaceutical compositions of the invention are administered in conjunction with other therapies, dosages of the co-administered compounds will of course vary depending on the type of co-drug employed, on the specific drug employed, on the condition being treated and so forth.

EXAMPLES

The following Examples are merely illustrative, and do not limit the scope of the invention otherwise claimed. The purity of reagents is analytical reagent grade or HPLC grade.

Abbreviations

XRPD X-ray powder diffraction
DSC Differential scanning calorimetry
TGA Thermogravimetric analysis
DVS Dynamic Vapor Sorption
RT room temperature
RH Relative humidity
THF Tetrahydrofuran
UPLC Ultra Performance Liquid Chromatography
FaSSIF Fasted State Simulated Intestinal Fluid
FeSSIF Fed State Simulated Intestinal Fluid
DVS Dynamic Vapor Sorption (DVS)
Instrumentation

| TGA-method | |
| --- | --- |
| Instrument | TA Discovery TGA Q5000 |
| Temperature range | 30° C.-300° C. |
| Scan rate | 10 K/min |
| Nitrogen flow | 25 mL/min |
| DSC-method | |
| Instrument | TA Discovery DSC |
| Temperature range | 30° C.-300° C. |
| Scan rate | 10 K/min |
| Nitrogen flow | 50 mL/min |
| XRPD-method | |
| Instrument | Bruker D8 Advance |
| Detector | LYNXEYE (1D mode), open angle: 1.996° |
| Radiation | CuKα (0.15 nm) |
| Monochromator | Nickel filter |
| X-ray generator power | 40 kV, 40 mA |
| Step size, resolution | 0.041 degree |
| Scan range | 2° to 45° (2 theta value) |
| Scan time | 1209 seconds |
| Source slit | Primary: fixed illuminated sample size 5 mm, secondary slit: 5 mm, axial soller: 2.5° |
| DVS | |
| Instrument | Intrinsic |
| Sample weight | About 5 mg |
| Temperature | 25° C. |
| dm/dt | 0.002%/min |

Example 1

Preparation of Compound I Fumaric Acid Co-Crystal (1:1) Form A

Ethyl acetate (1 mL) was added to Compound I (50 mg) at 55° C. and stirred at 500 rpm for 2 hrs, to which was added fumaric acid (1 eq., 13.1 mg). The reaction mixture was stirred at 55° C. for 5 hrs, cooled to RT over a 4 hr period, and stirred for another 12 hrs. The resulting solids were filtered and dried at 55° C. under vacuum for 6 hrs to give Compound I fumaric acid co-crystal (1:1) Form A ("Form A").

Figure 2:
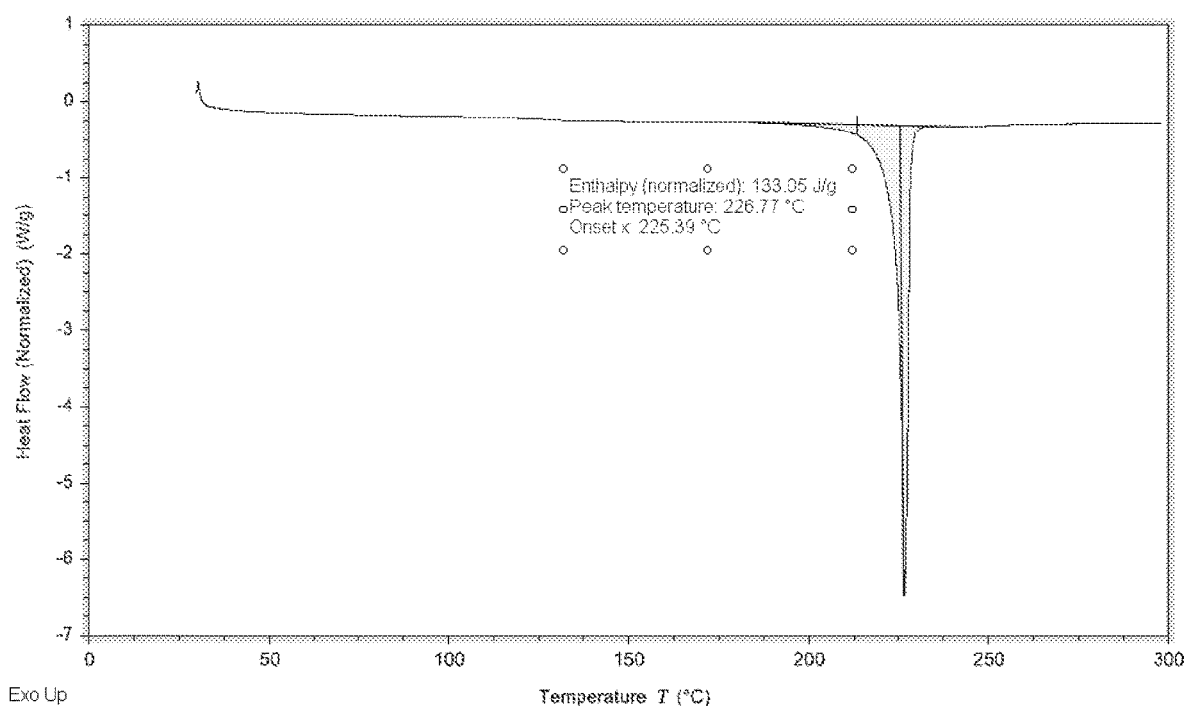
FIG. 2 shows a differential scanning calorimetry (DSC) curve of Compound I fumaric acid co-crystal (1:1) Form A.
Figure 3:
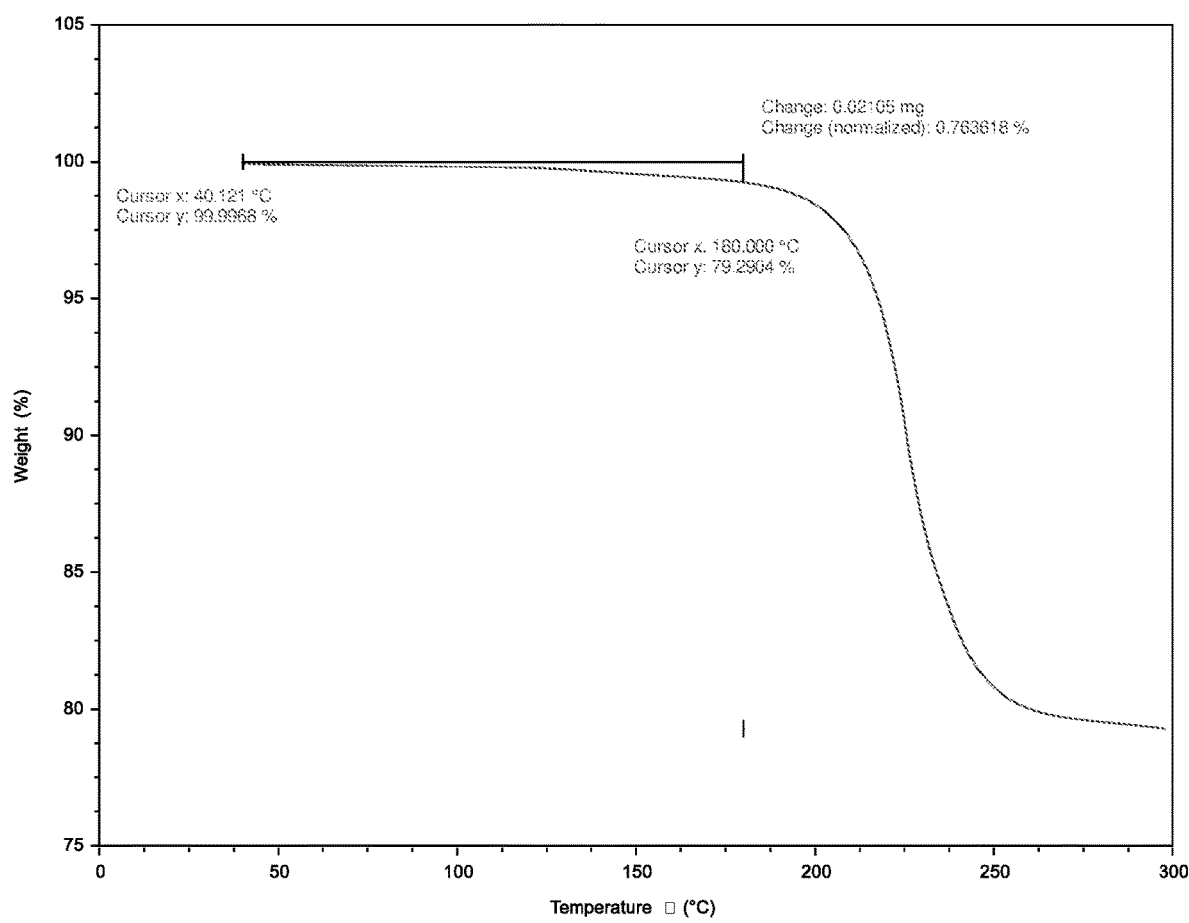
FIG. 3 shows a thermogravimetric (TGA) plot of Compound I fumaric acid co-crystal (1:1) Form A.

Form A is characterized by one or more of the following parameters: (a) an X-ray powder diffraction pattern that is substantially as shown in FIG. 1 with corresponding peaks listed in Table 1 when measured with a CuKα radiation at a wavelength of 0.15 nm at room temperature; (b) a differential scanning calorimetry (DSC) thermogram that is substantially as shown in FIG. 2 when heated from 30 to 300° C. at a rate of 10 K/min; and a thermogravimetric analysis (TGA) diagram that is substantially as shown in FIG. 3 when heated from 30 to 300° C. at a rate of 10 K/min. In one embodiment, Form A is characterized by an X-ray powder diffraction pattern comprising three or more 2θ peaks selected from about 9.4°, 11.0°, 14.2° and 25.8°. Form A has a melting point onset at 225.4° C. by DSC and an enthalpy of fusion of 127 J/g.

TABLE 1

| Angle °2θ | d value Å | Rel. | Intensity description |
|---|---|---|---|
| 4.6 | 19.28 | 3.2% | weak |
| 5.0 | 17.53 | 17.3% | weak |
| 9.4 | 9.38 | 48.7% | medium |
| 10.1 | 8.73 | 5.1% | weak |
| 11.0 | 8.06 | 27.6% | medium |
| 13.4 | 6.59 | 15.0% | weak |
| 13.5 | 6.58 | 15.9% | weak |
| 14.2 | 6.21 | 28.2% | medium |
| 15.2 | 5.82 | 6.0% | weak |
| 17.1 | 5.19 | 8.7% | weak |
| 18.6 | 4.76 | 17.6% | weak |
| 19.0 | 4.68 | 8.5% | weak |
| 19.3 | 4.60 | 7.9% | weak |
| 19.7 | 4.49 | 11.3% | weak |
| 19.8 | 4.49 | 9.3% | weak |
| 22.0 | 4.04 | 6.6% | weak |
| 23.0 | 3.86 | 11.1% | weak |
| 23.4 | 3.80 | 7.7% | weak |
| 24.2 | 3.67 | 11.2% | weak |
| 24.8 | 3.59 | 10.5% | weak |
| 25.8 | 3.45 | 100% | strong |
| 28.8 | 3.10 | 13.6% | weak |

Example 2A

Preparation of Compound I Fumaric Acid Co-Crystal (1:1) Form B by Form a Seeding Ethyl acetate (60 mL) was added to Compound I (3 g) at 55° C. and stirred at 500 r.p.m. for 2 hours, to which was added fumaric acid (1 eq, 796 mg). The reaction mixture was stirred at 55° C. for 6 hours, to which was added a small amount of Form A prepared in Example 1 (20 mg). The reaction mixture seeded with Form A was stirred at 55° C. for 16 hours, cooled to RT over a 2 hour period, and stirred for 8 hours. The resulting solids were filtered, washed with ethyl acetate (5 mL), and dried at 55° C. under vacuum for 12 hours to give Compound I fumaric acid co-crystal (1:1) Form B ("Form B").

Example 2B

Preparation of Compound I Fumaric Acid Co-Crystal (1:1) Form B Seeds

THF (200 mL) was added to Compound I (20 g, 45.1 mmol, 1 eq) at RT to form a Compound I/THF suspension. Fumaric acid (5.8 g, 49.6 mmol, 1.1 eq) was added to isopropyl alcohol (160 mL) at RT, and the resulting fumaric acid solution was added to the Compound I/THF suspension over a 1 hr period. The reaction mixture was stirred at RT for 20 hrs, filtered, and the filter cake was washed with isopropyl alcohol (40 mL). The collected solids were dried at 50° C. under vacuum for 20 hrs, and equilibrated in ethyl acetate (100 mL) at 50° C. for 30 hrs. The solids were filtered and dried under vacuum at 50° C. for 16 h to give Form B, which was used as fumarate seed crystals.

Example 2C

Preparation of Compound I Fumaric Acid Co-Crystal (1:1) Form B by Form B Seeding Fumaric acid (6.0 g, 51.9 mmol, 1.15 eq) was added to isopropyl alcohol (130 mL). The resulting solution was heated to 52° C., and filtered to obtain a clear fumaric acid solution. The fumaric acid solution was maintained at 50° C., to which was added a small amount of Form B prepared in Example 2B (10 mg) to give a fumaric acid solution seeded with Form B.

Compound I (20 g, 45.1 mmol, 1 eq) was added to THF (500 mL) at RT; and the resulting suspension was heated to 55° C. to obtain a clear solution, which was subsequently filtered. The filtrate was partially concentrated under vacuum, and the residual compound (287 g) was added dropwise to the fumaric acid solution seeded with Form B over a 1 hr period at 50° C. The reaction mixture was maintained at 50° C. for 2 hrs, subsequently cooled to RT over a 5-7 hr period, then concentrated under vacuum at 50° C. Isopropyl alcohol (200 mL*3) was added to the concentrate to further remove residual THF. The resulting suspension was cooled to RT over a 2-4 hr period, filtered and washed with pre-cooled isopropyl alcohol (40 mL). The solid was dried at 60° C. under vacuum for 16 hrs to give Form B as an off-white solid. $^1$H NMR (400 MHz, DMSO-$d_6$) δ ppm 2.40 (s, 3H), 6.64 (s, 2H), 7.41-7.45 (m, 1H), 7.82 (br d, J=0.73 Hz, 1H), 7.87-8.00 (m, 1H), 8.59 (dd, J=4.65, 1.10 Hz, 1H), 8.79 (dd, J=6.66, 2.75 Hz, 1H), 9.14 (d, J=2.45 Hz, 1H), 9.75 (d, J=2.32 Hz, 1H), 10.35-10.44 (m, 1H); $^{13}$C NMR (101 MHz, DMSO-$d_6$) δ ppm 13.24, 14.25, 19.78, 117.34, 117.56, 118.34, 118.45, 122.84, 122.86, 124.02, 124.18, 124.70, 124.78, 132.79, 134.42, 135.44, 135.47, 136.76, 139.16, 139.67, 143.45, 147.86, 151.16, 154.70, 155.46, 156.78, 157.18, 157.98, 161.42, 162.38, 162.44, 166.42; MS m/z=444.9 (M+H$^+$).

Figure 4:
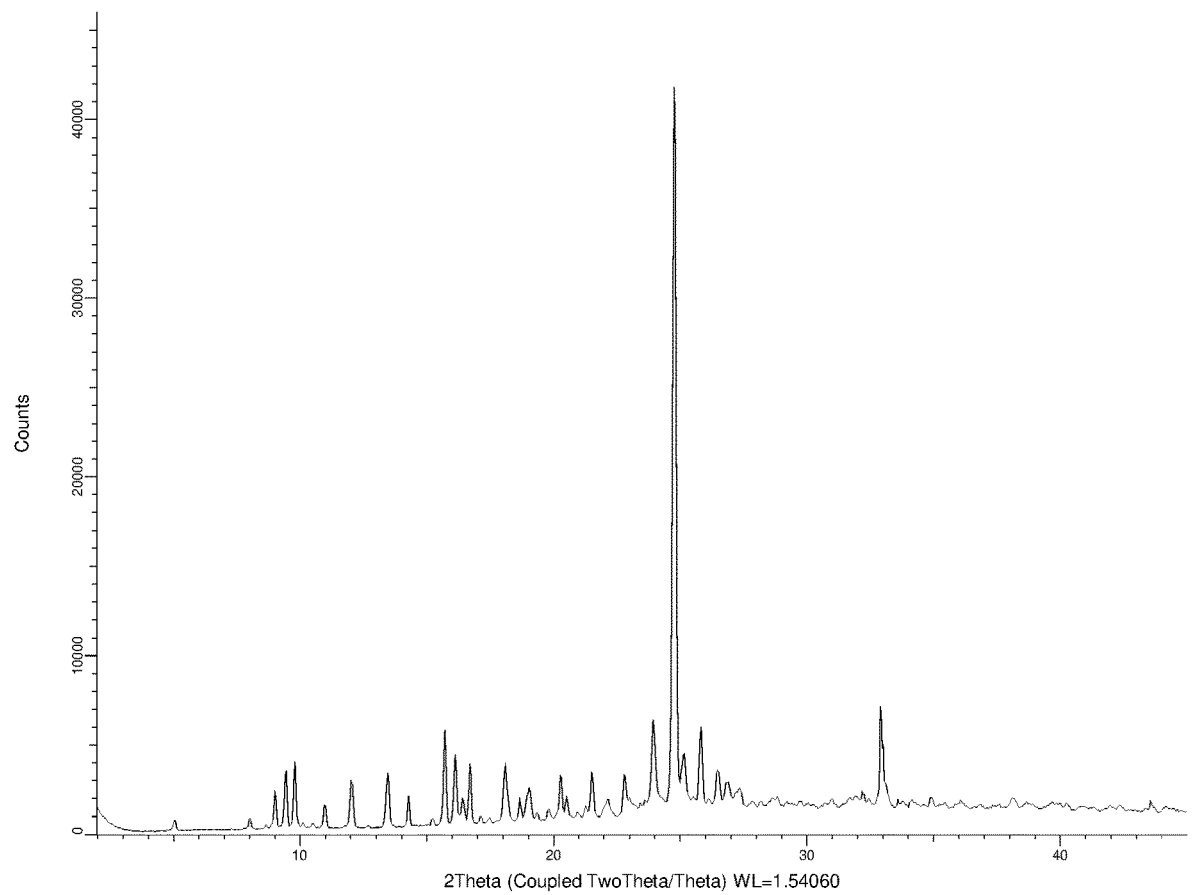
FIG. 4 shows an XRPD pattern of Compound I fumaric acid co-crystal (1:1) Form B.
Figure 5:
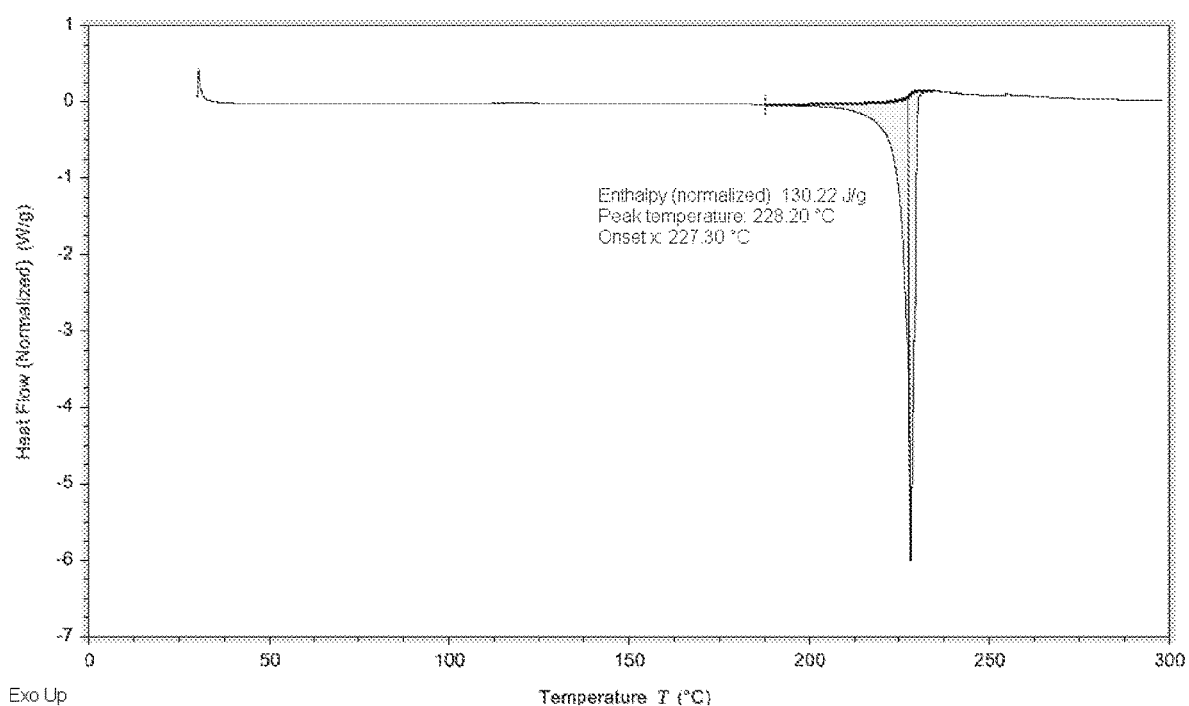
FIG. 5 shows a DSC curve of Compound I fumaric acid co-crystal (1:1) Form B.
Figure 6:
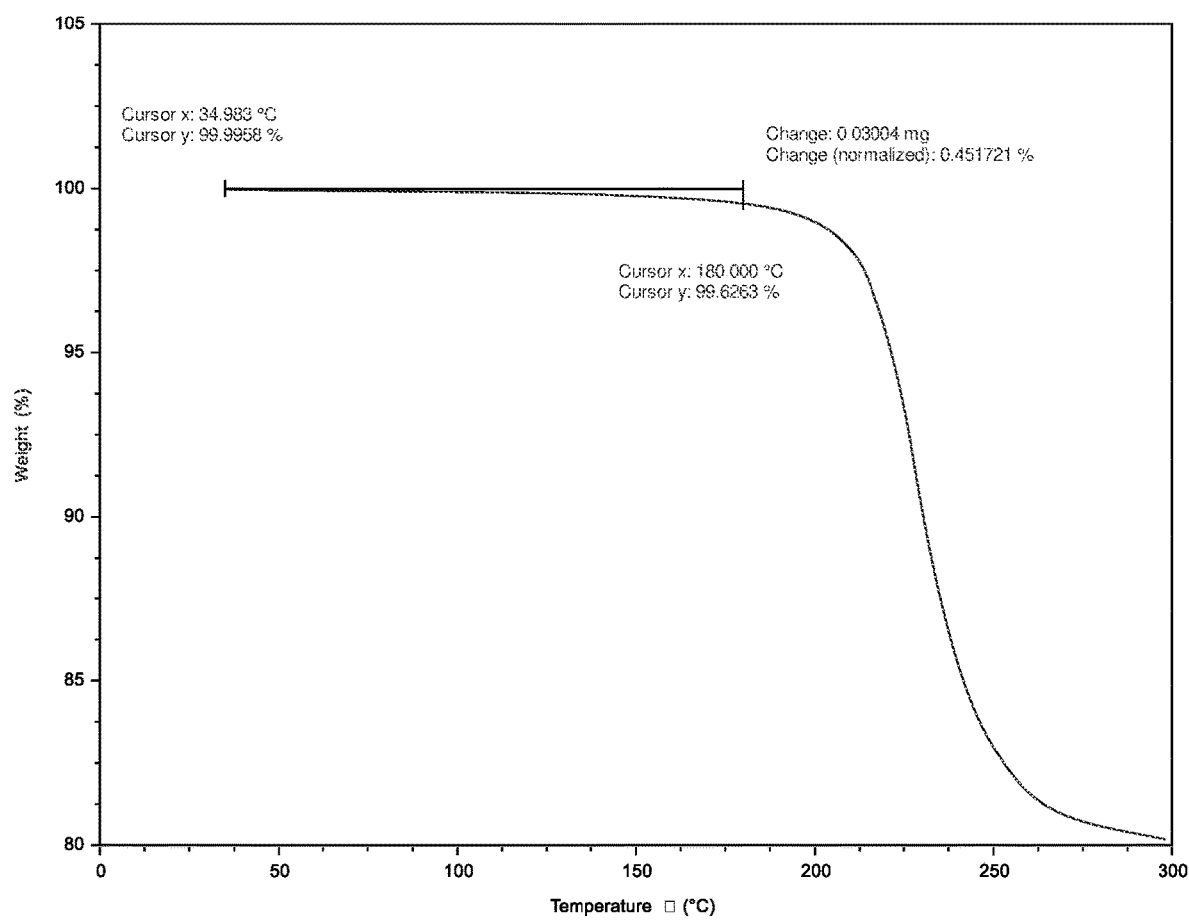
FIG. 6 shows a TGA plot of Compound I fumaric acid co-crystal (1:1) Form B.

Form B is characterized by one or more of the following parameters: (a) an X-ray powder diffraction pattern that is substantially as shown in FIG. 4 with corresponding peaks listed in Table 2 when measured with a CuKα radiation at a wavelength of 0.15 nm at room temperature; (b) a differential scanning calorimetry (DSC) thermogram that is substantially as shown in FIG. 5 when heated from 30 to 300° C. at a rate of 10 K/min; and a thermogravimetric analysis (TGA) diagram that is substantially as shown in FIG. 6 when heated from 30 to 300° C. at a rate of 10 K/min. In one embodiment, Form B is characterized by an X-ray powder diffraction pattern comprising three or more 2θ peaks selected from about 13.4°, 15.7°, 23.9° and 24.7°.

Form B has a melting point onset at 227.3° C. by DSC and 0.5% weight loss at 180° C. by TGA. Form B is non-hygroscopic and absorbs 0.3% moisture at 90% RH at 25° C. by DVS. Form B shows stability and solubility (24 h) in aqueous media comparable to the free form hydrate.

TABLE 2

| Angle °2θ | d value Å | Rel. | Intensity |
|---|---|---|---|
| 8.0 | 11.10 | 7.0% | weak |
| 9.0 | 9.86 | 12.8% | weak |
| 9.4 | 9.44 | 7.5% | weak |
| 9.4 | 9.43 | 7.3% | weak |

TABLE 2-continued

| Angle °2θ | d value Å | Rel. | Intensity |
|---|---|---|---|
| 9.8 | 9.06 | 17.6% | weak |
| 12.1 | 7.32 | 8.3% | weak |
| 12.0 | 7.37 | 16.1% | weak |
| 13.4 | 6.60 | 22.3% | medium |
| 16.0 | 5.65 | 23.3% | medium |
| 16.1 | 5.52 | 17.7% | weak |
| 16.4 | 5.41 | 7.8% | weak |
| 16.6 | 5.33 | 14.7% | weak |
| 18.1 | 4.91 | 15.1% | weak |
| 19.0 | 4.67 | 11.8% | weak |
| 20.2 | 4.39 | 17.0% | weak |
| 20.4 | 4.34 | 12.5% | weak |
| 21.2 | 4.19 | 7.3% | weak |
| 22.1 | 4.02 | 5.0% | weak |
| 22.7 | 3.91 | 12.6% | weak |
| 22.8 | 3.90 | 12.8% | weak |
| 23.6 | 3.77 | 3.1% | weak |
| 23.9 | 3.72 | 24.2% | medium |
| 24.7 | 3.60 | 100.0% | strong |
| 25.1 | 3.55 | 11.2% | weak |
| 26.4 | 3.37 | 6.9% | weak |
| 32.9 | 2.72 | 5.8% | weak |
| 34.8 | 2.57 | 3.9% | weak |

Example 3

Preparation of Compound I Fumaric Acid Co-Crystal (1:1) Form C

Form B (500 mg) was equilibrated in acetone (6 mL) at 50° C. for 72 hrs. The solids were filtered at RT and dried under vacuum at 40° C. for 18 h to give Compound I fumaric acid co-crystal (1:1) Form C ("Form C").

Figure 7:
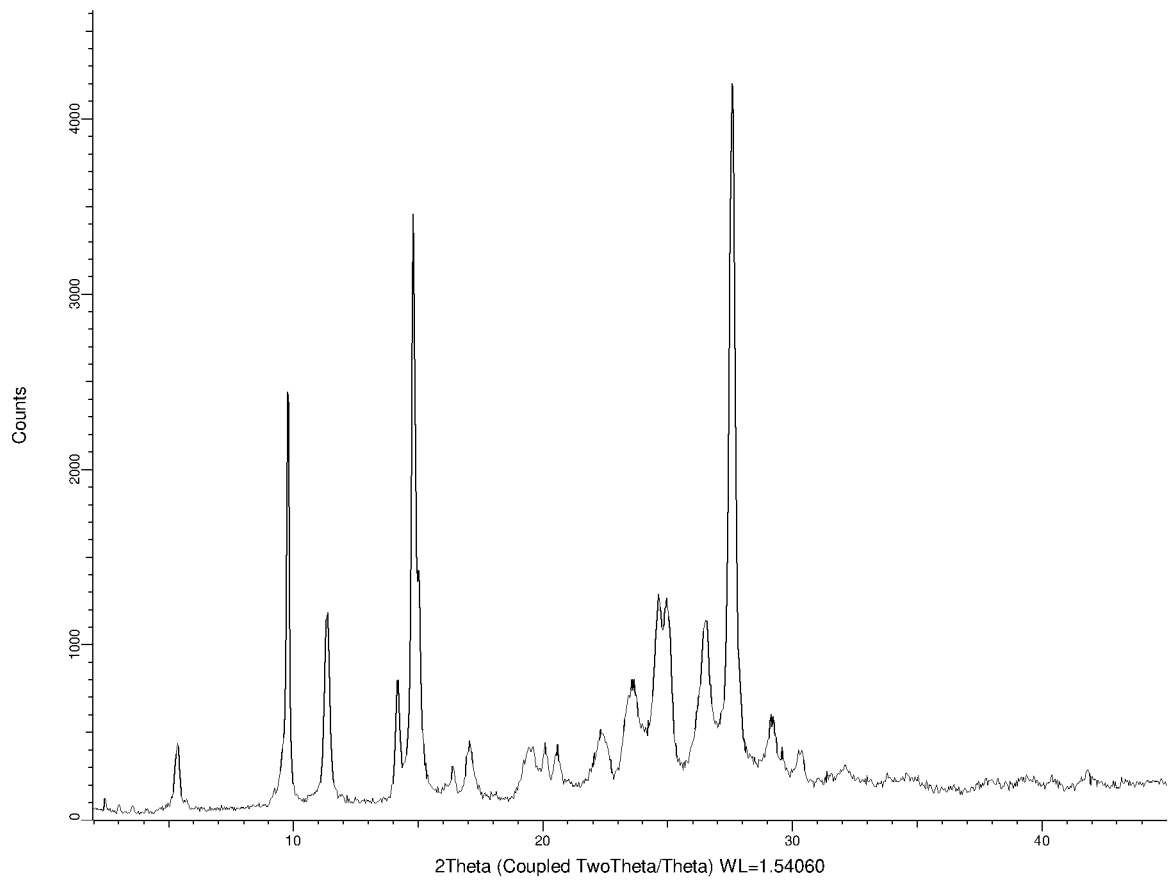
FIG. 7 shows an XRPD pattern of Compound I fumaric acid co-crystal (1:1) Form C.
Figure 8:
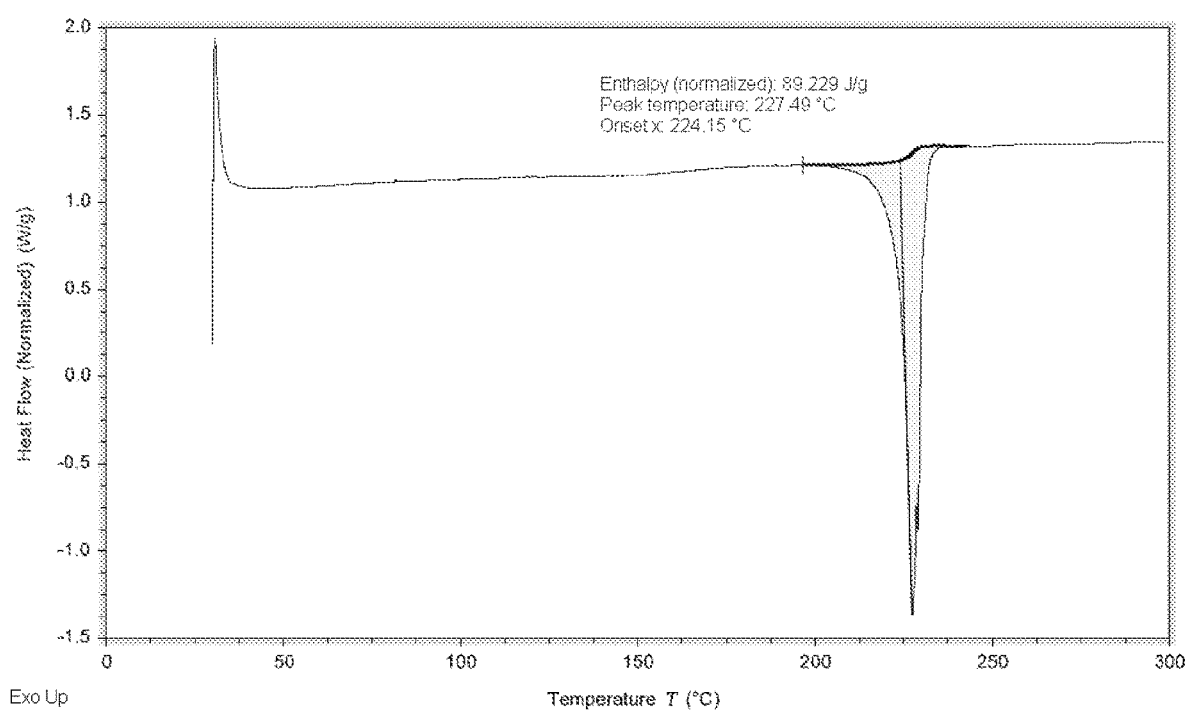
FIG. 8 shows a DSC curve of Compound I fumaric acid co-crystal (1:1) Form C.
Figure 9:
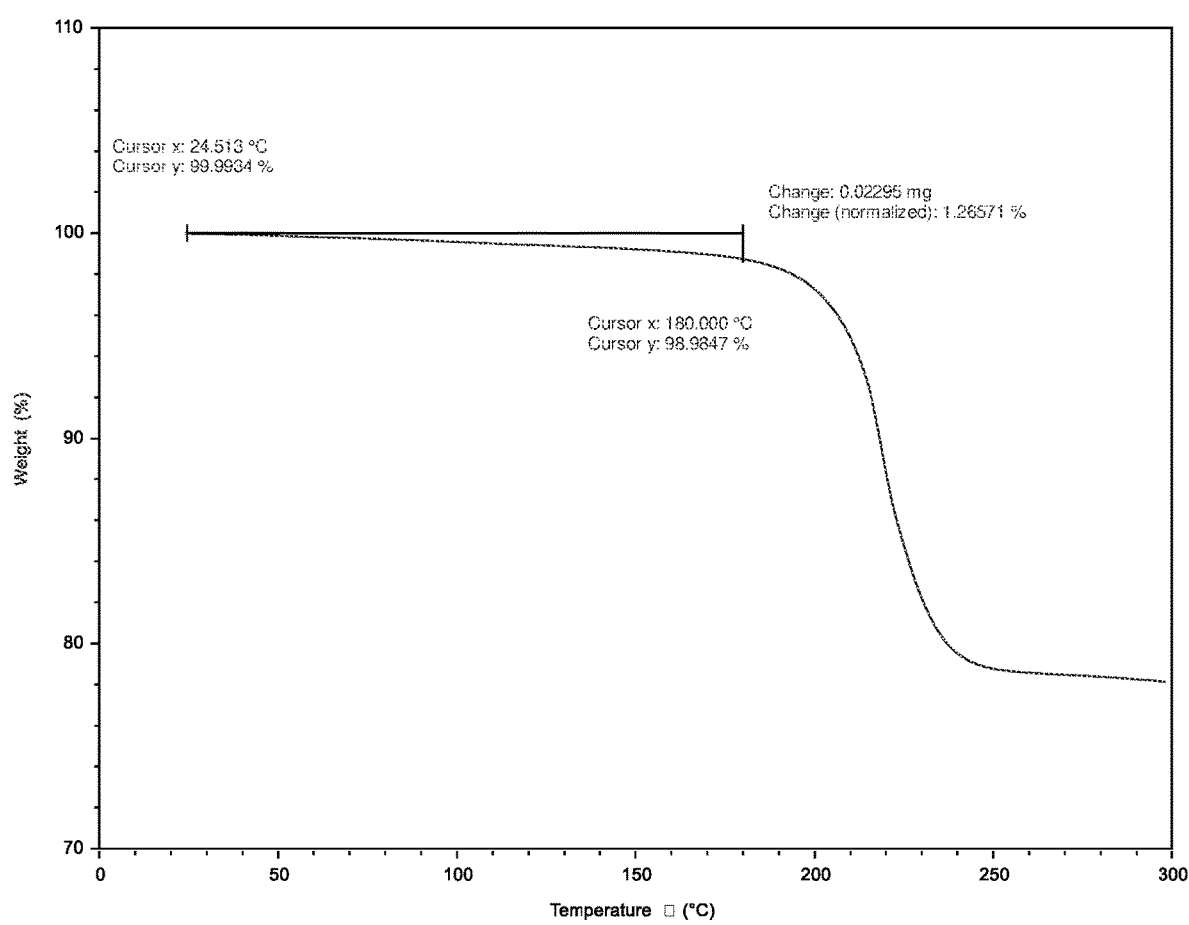
FIG. 9 shows a TGA plot of Compound I fumaric acid co-crystal (1:1) Form C.

Form C is characterized by one or more of the following parameters: (a) an X-ray powder diffraction pattern that is substantially as shown in FIG. 7 with corresponding peaks listed in Table 3 when measured with a CuKα radiation at a wavelength of 0.15 nm at room temperature; (b) a differential scanning calorimetry (DSC) thermogram that is substantially as shown in FIG. 8 when heated from 30 to 300° C. at a rate of 10 K/min; and a thermogravimetric analysis (TGA) diagram that is substantially as shown in FIG. 9 when heated from 30 to 300° C. at a rate of 10 K/min. In one embodiment, Form C is characterized by an X-ray powder diffraction pattern comprising three or more 2θ peaks selected from about 9.8°, 11.3°, 14.8°, 24.6°, 25.0°, 26.5° and 27.6°.

Form C has a melting point onset at 219.2° C. by DSC and 1.3% weight loss at 180° C. by TGA. Form C is slightly hygroscopic and reversibly absorbs approximately 0.6% moisture at 90% RH by DVS.

TABLE 3

| Angle °2θ | d value Å | Rel. intensity | Intensity |
|---|---|---|---|
| 5.4 | 16.47 | 9.8% | weak |
| 9.8 | 9.04 | 55.9% | medium |
| 11.3 | 7.79 | 26.9% | medium |
| 14.2 | 6.25 | 17.2% | weak |
| 14.8 | 5.97 | 82.3% | strong |
| 16.4 | 5.41 | 3.8% | weak |
| 17.1 | 5.19 | 7.5% | weak |
| 19.6 | 4.53 | 6.3% | weak |
| 20.6 | 4.31 | 5.4% | weak |
| 22.4 | 3.97 | 6.3% | weak |
| 23.6 | 3.78 | 11.3% | weak |
| 23.6 | 3.76 | 11.6% | weak |
| 24.6 | 3.61 | 24.1% | medium |

TABLE 3-continued

| Angle °2θ | d value Å | Rel. intensity | Intensity |
|---|---|---|---|
| 25.0 | 3.56 | 23.9% | medium |
| 26.5 | 3.358 | 20.8% | medium |
| 27.6 | 3.23 | 100.0% | strong |
| 29.2 | 3.06 | 6.3% | weak |
| 30.2 | 2.96 | 2.8% | weak |

Example 4

Preparation of Compound I Fumaric Acid Co-Crystal (2:1) by Form B Seeding

Compound I (22.5 g, 50.7 mmol, 1 eq) was added to THF (450 mL) at RT; and the resulting suspension was heated to 55° C. to obtain a clear solution, which was subsequently filtered. The filtrate was partially concentrated under vacuum to give a residue comprising Compound I and THF (202.5 g).

Fumaric acid (6.5 g, 55.8 mmol, 1.1 eq) was added to isopropyl alcohol (225 mL). The resulting solution was heated to 52° C., filtered to obtain a clear fumaric acid solution, and added dropwise into the residue comprising Compound I and THF. After half of the fumaric acid solution was added to the residue comprising Compound I and THF over a 1 hr period, a small amount of Form B prepared in Example 2B (11.3 mg) was added to the remaining fumaric acid solution. The remaining fumaric acid solution was added to the reaction mixture over a 2 hr period.

The reaction mixture was maintained at 50° C. for 2 hrs, subsequently cooled to RT over a 5-7 hr period, then concentrated under vacuum at 50° C. Isopropyl alcohol (225 mL*2) was added to the concentrate to further remove residual THF. The resulting suspension was cooled to RT over a 2-4 hr period, filtered and washed with pre-cooled isopropyl alcohol (45 mL). The solid was dried at 60° C. under vacuum for 16 hrs to give Compound I fumaric acid co-crystal (2:1) as an off-white solid. $^1$H NMR (400 MHz, DMSO-$d_6$) δ ppm 2.41 (s, 3H), 6.63 (s, 1H), 7.43-7.46 (m, 1H), 7.85 (dd, J=7.70, 0.73 Hz, 1H), 7.91-7.99 (m, 1H), 8.61 (dd, J=4.65, 0.98 Hz, 1H), 8.80 (dd, J=6.66, 2.75 Hz, 1H), 9.15 (d, J=2.45 Hz, 1H), 9.76 (d, J=2.32 Hz, 1H), 10.35-10.48 (m, 1H); $^{13}$C NMR (101 MHz, DMSO-$d_6$) δ ppm 13.26, 14.28, 19.77, 117.38, 117.61, 118.37, 118.48, 122.87, 124.05, 124.22, 124.74, 124.82, 132.83, 134.49, 135.45, 135.48, 136.79, 139.18, 139.70, 143.47, 147.89, 151.19, 154.72, 155.48, 156.82, 157.21, 157.98, 161.46, 162.37, 162.43, 166.50; MS m/z=444.9 (M+H$^+$).

Figure 10:
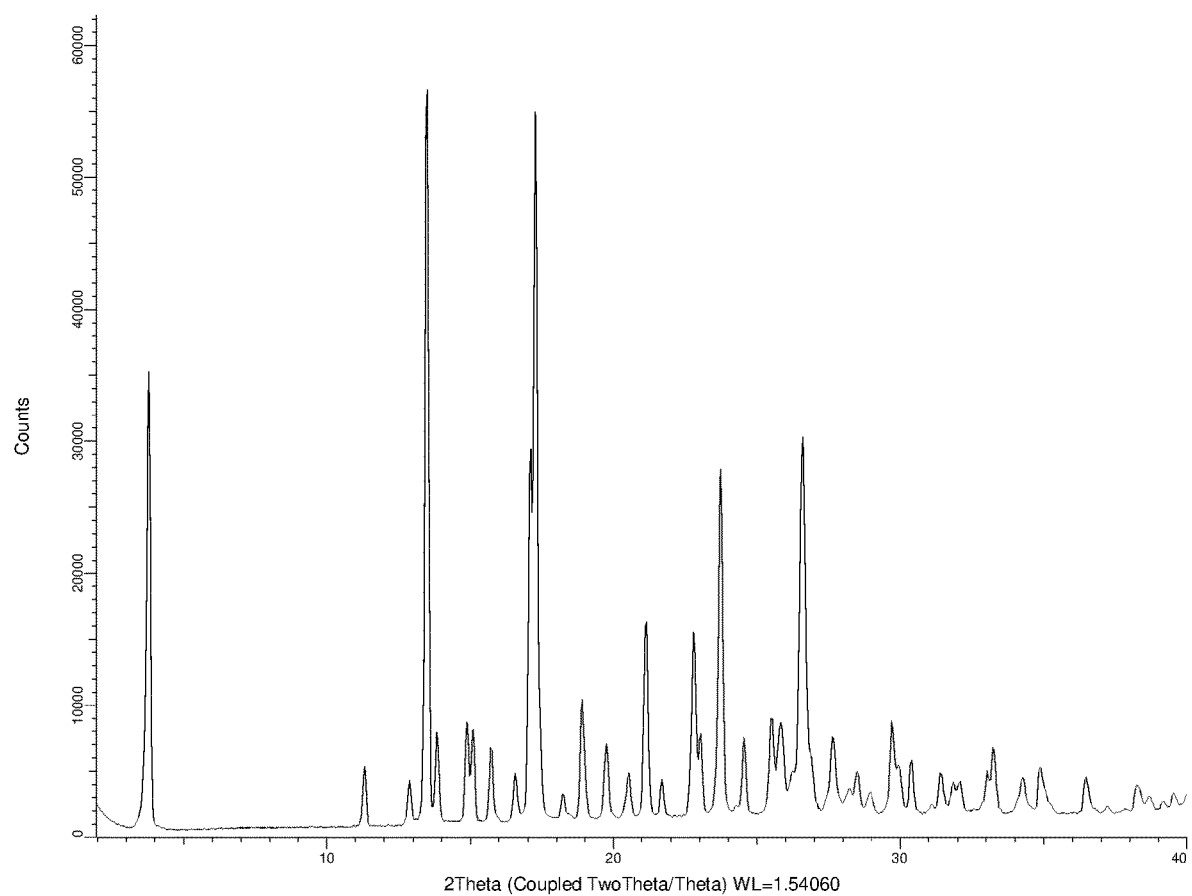
FIG. 10 shows an XRPD pattern of Compound I fumaric acid co-crystal (2:1).
Figure 11:
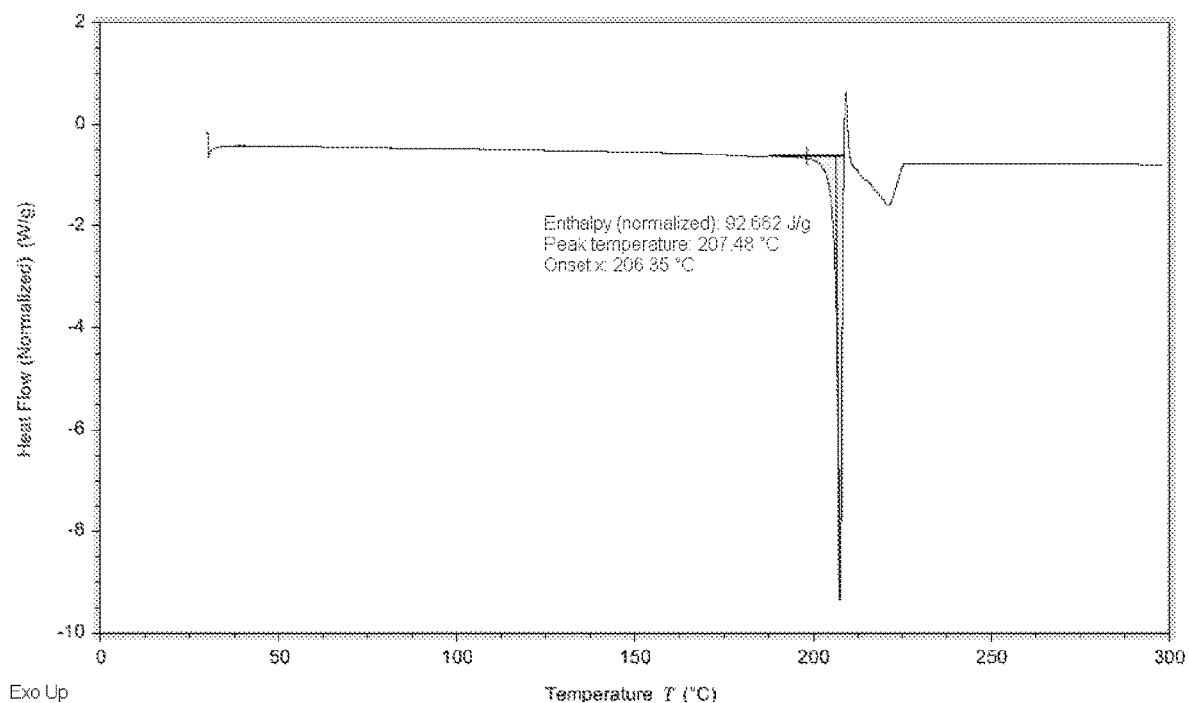
FIG. 11 shows a DSC curve of Compound I fumaric acid co-crystal (2:1).
Figure 12:
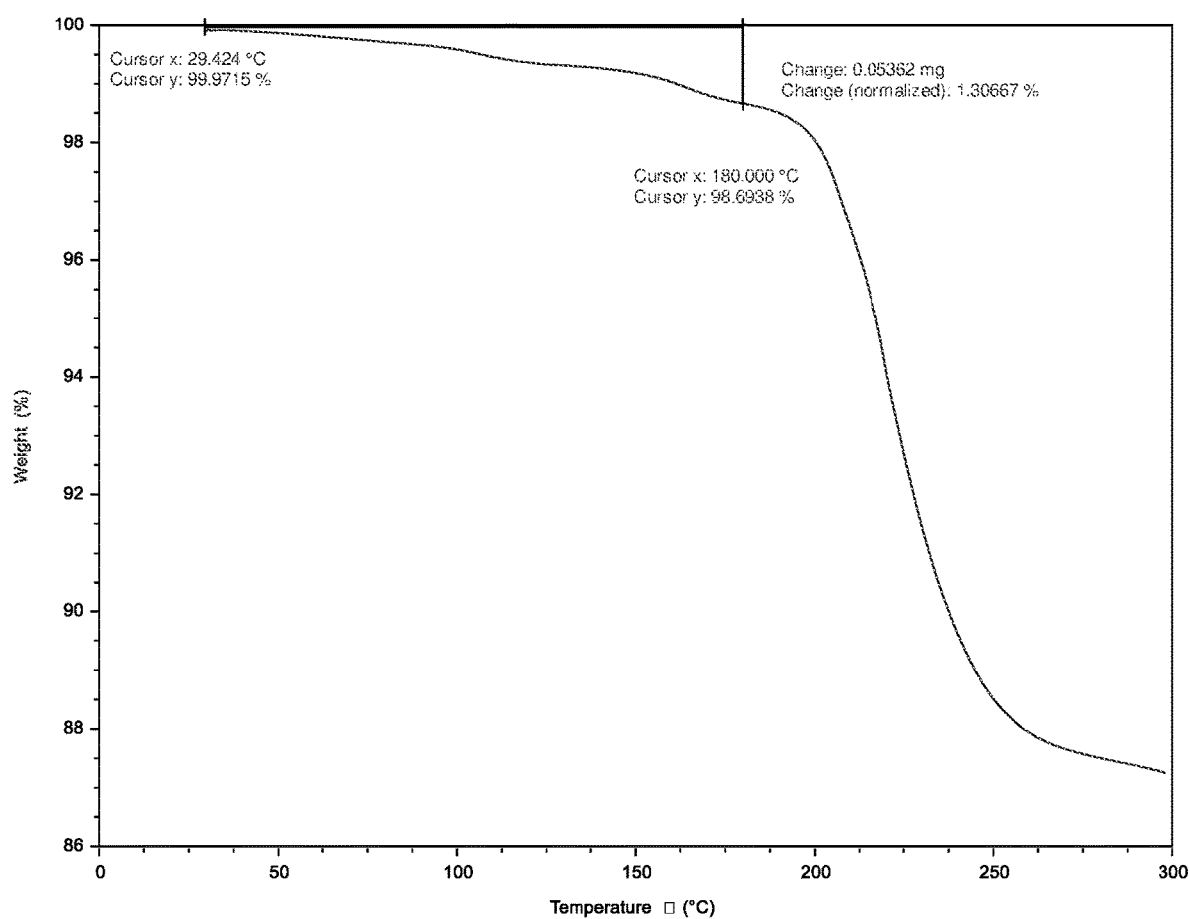
FIG. 12 shows a TGA plot of Compound I fumaric acid co-crystal (2:1).

Compound I fumaric acid co-crystal (2:1) are characterized by one or more of the following parameters: (a) an X-ray powder diffraction pattern that is substantially as shown in FIG. 10 with corresponding peaks listed in Table 4 when measured with a CuKα radiation at a wavelength of 0.15 nm at room temperature; (b) a differential scanning calorimetry (DSC) thermogram that is substantially as shown in FIG. 11 when heated from 30 to 300° C. at a rate of 10 K/min; and (c) a thermogravimetric analysis (TGA) diagram that is substantially as shown in FIG. 12 when heated from 30 to 300° C. at a rate of 10 K/min. In one embodiment, Compound I fumaric acid co-crystal (2:1) are characterized by an X-ray powder diffraction pattern comprising three or more 2θ peaks selected from about 3.8°, 13.5°, 17.2° and 26.6°.

Compound I fumaric acid co-crystal (2:1) have a melting point onset at 206.4° C. by DSC and 1.3% weight loss up to 180° C. by TGA. Compound I fumaric acid co-crystal (2:1) are non-hygroscopic and absorb only 0.12% at 90% RH at 25° C. by DVS.

TABLE 4

| Angle °2θ | d value Å | Rel. intensity | Intensity description |
|---|---|---|---|
| 3.8 | 23.48 | 60.6% | strong |
| 11.3 | 7.80 | 8.7% | weak |
| 12.9 | 6.85 | 5.7% | weak |
| 13.5 | 6.55 | 100.0% | strong |
| 15.0 | 5.91 | 6.8% | weak |
| 15.8 | 5.62 | 10.5% | weak |
| 16.6 | 5.32 | 4.5% | weak |
| 17.2 | 5.14 | 81.5% | strong |
| 18.3 | 4.85 | 2.2% | weak |
| 18.9 | 4.69 | 17.3% | weak |
| 19.8 | 4.49 | 10.8% | weak |
| 20.5 | 4.32 | 6.2% | weak |
| 21.2 | 4.20 | 28.6% | medium |
| 21.7 | 4.09 | 5.0% | weak |
| 22.9 | 3.88 | 17.6% | weak |
| 23.7 | 3.74 | 50.3% | medium |
| 24.5 | 3.63 | 9.6% | weak |
| 25.7 | 3.46 | 9.7% | weak |
| 26.6 | 3.35 | 55.0% | medium |
| 27.7 | 3.22 | 8.8% | weak |
| 28.4 | 3.14 | 2.8% | weak |
| 29.8 | 2.99 | 7.6% | weak |
| 30.4 | 2.95 | 6.2% | weak |
| 31.4 | 2.84 | 5.5% | weak |
| 31.9 | 2.80 | 3.5% | weak |
| 33.2 | 2.70 | 5.1% | weak |
| 34.3 | 2.61 | 5.1% | weak |
| 35.0 | 2.56 | 5.6% | weak |
| 36.5 | 2.46 | 4.6% | weak |

Example 5

Preparation of Amorphous Compound I Fumaric Acid (1:1)

Compound I fumaric acid co-crystal (1:1) Form B seeds (100 mg), prepared following the procedure in Example 2B, was dissolved in 1,4-dioxane (30 mL). The resulting suspension was filtered, and the filtrate was frozen using an acetone dry ice bath. The frozen filtrate was freeze-dried for 3 days at −20° C. to provide amorphous Compound I fumaric acid (1:1).

Figure 13:
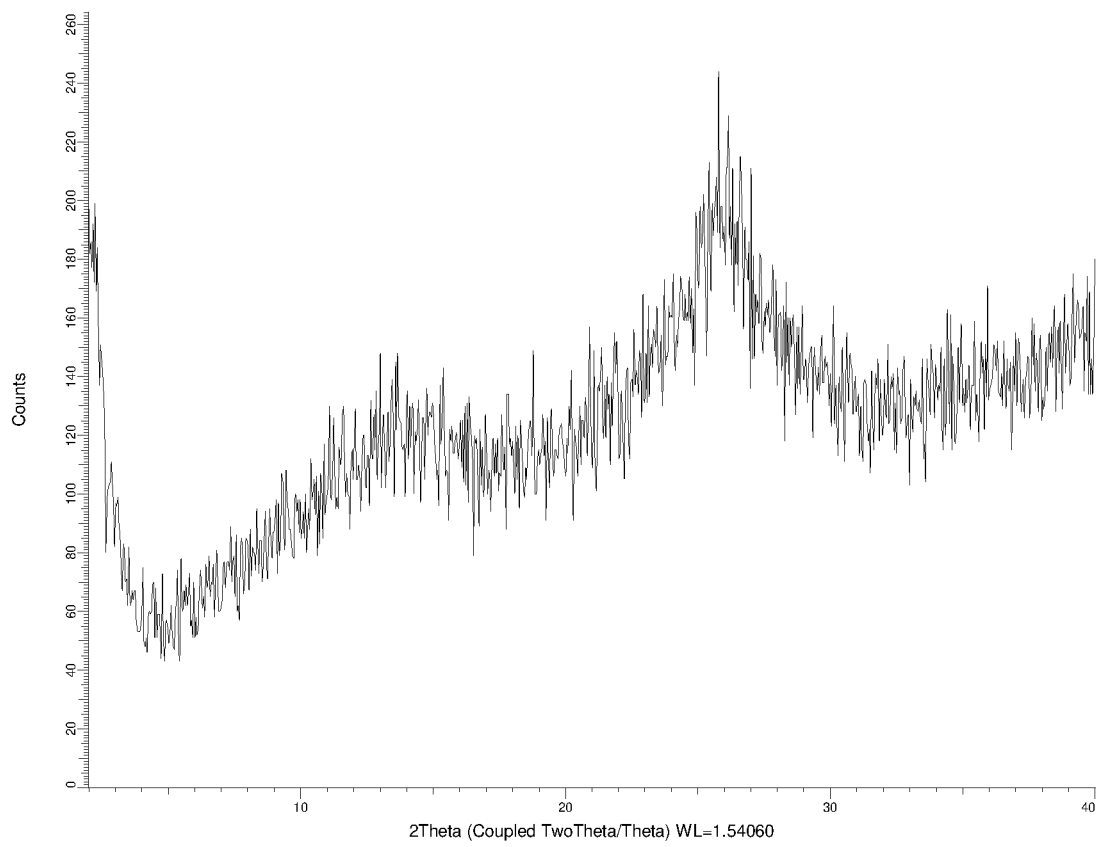
FIG. 13 shows an XRPD pattern of an X-ray amorphous complex of Compound I and fumaric acid (1:1).
Figure 14:
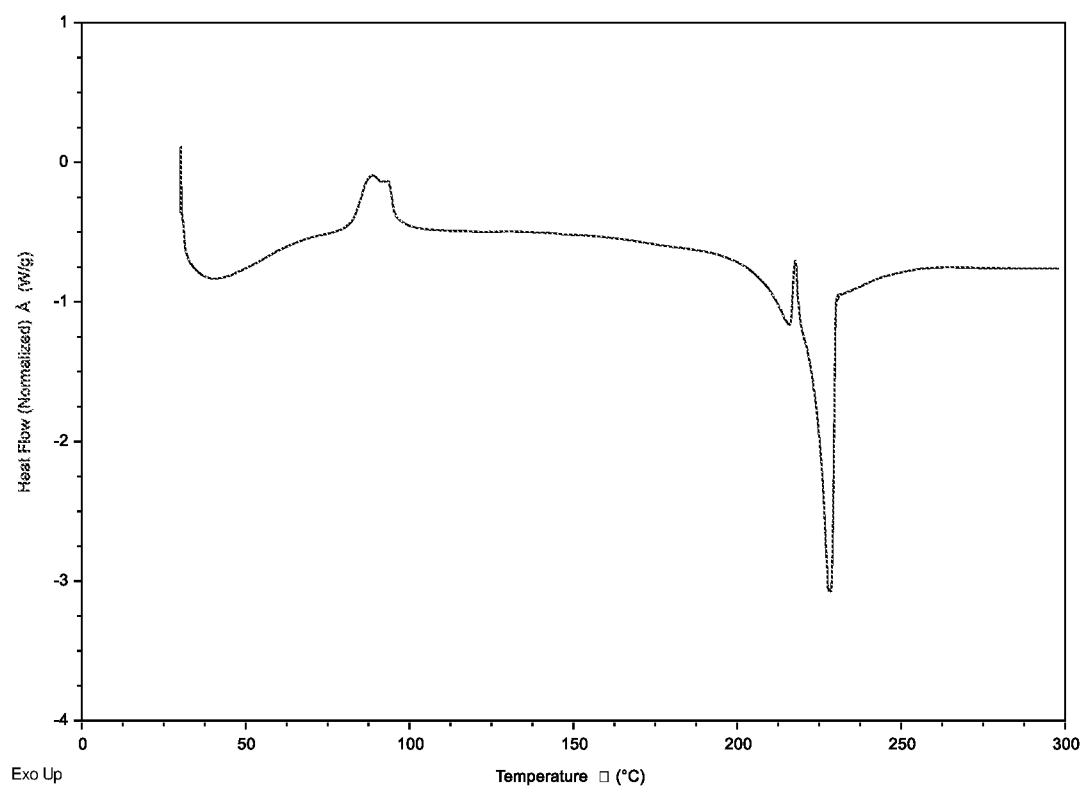
FIG. 14 shows a DSC curve of an X-ray amorphous complex of Compound I and fumaric acid (1:1).
Figure 15:
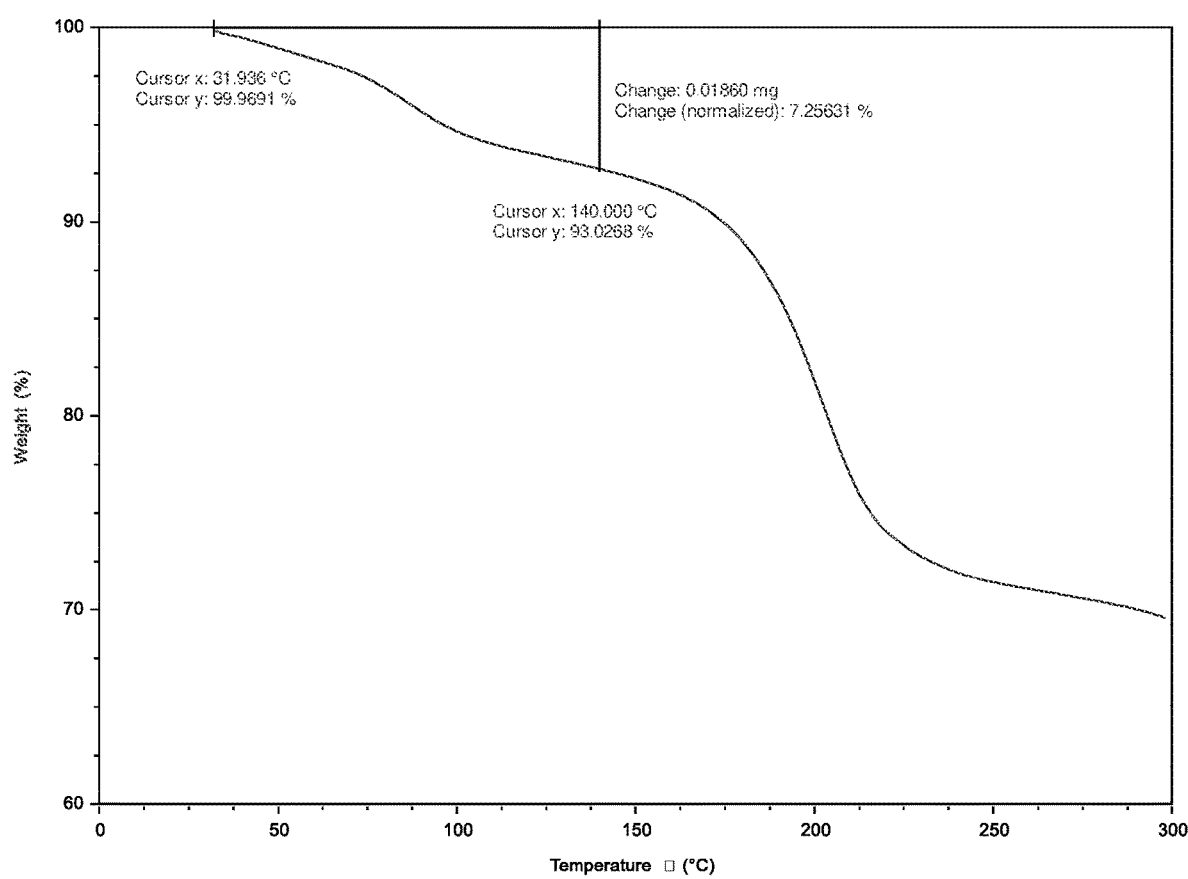
FIG. 15 shows a TGA plot of an X-ray amorphous complex of Compound I and fumaric acid (1:1).

The amorphous Compound I fumaric acid (1:1) is characterized by one or more of the following parameters: (a) an X-ray powder diffraction pattern that is substantially as shown in FIG. 13, showing no well-defined peaks when measured with a CuKα radiation at a wavelength of 0.15 nm at room temperature; (b) a differential scanning calorimetry (DSC) thermogram that is substantially as shown in FIG. 14 when heated from 30 to 300° C. at a rate of 10 K/min; and (c) a thermogravimetric analysis (TGA) diagram that is substantially as shown in FIG. 15 when heated from 30 to 300° C. at a rate of 10 K/min.

Example 6

Preparation of Amorphous Compound I Fumaric Acid (2:1)

Compound I fumaric acid co-crystal (2:1) (100 mg), prepared following the procedure in Example 4, was dissolved in 1,4-dioxane (15 mL). The resulting suspension was filtered, and the filtrate was frozen using an acetone dry ice bath. The frozen filtrate was freeze-dried for 3 days at −20° C. to provide amorphous Compound I fumaric acid (2:1).

Figure 16:
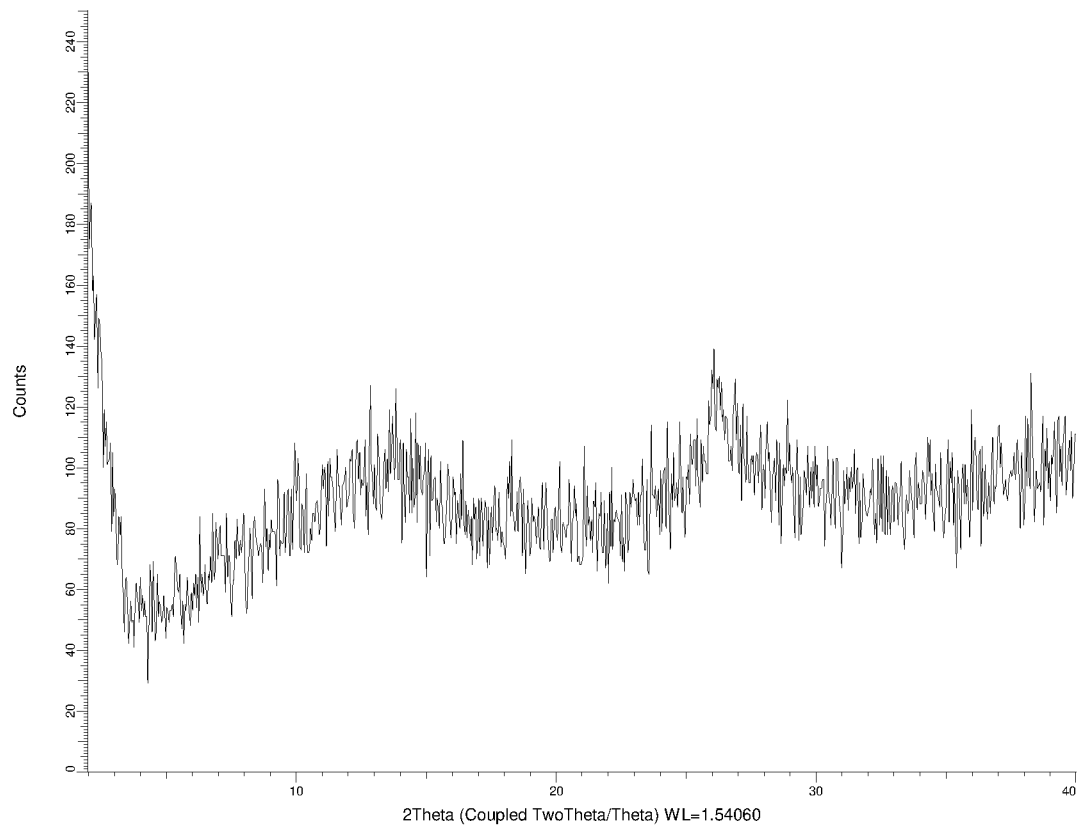
FIG. 16 shows an XRPD pattern of an X-ray amorphous complex of Compound I and fumaric acid (2:1).
Figure 17:
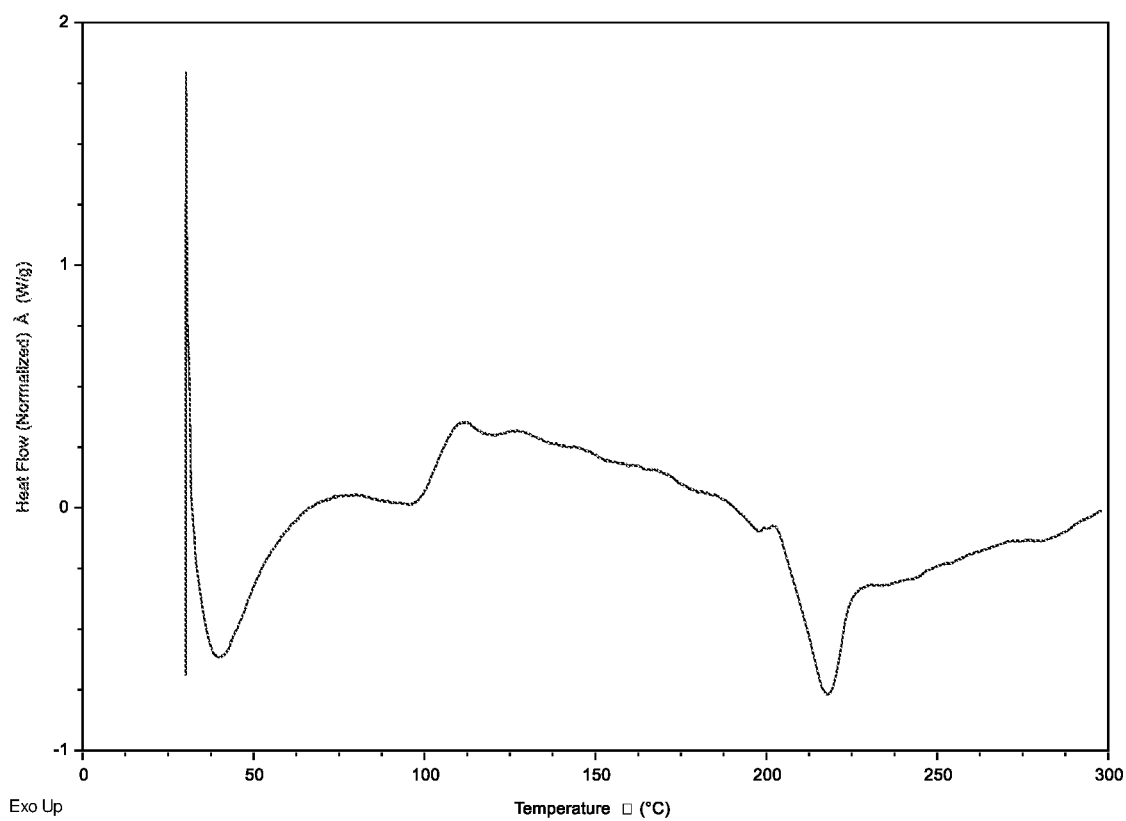
FIG. 17 shows a DSC curve of an X-ray amorphous complex of Compound I and fumaric acid (2:1).
Figure 18:
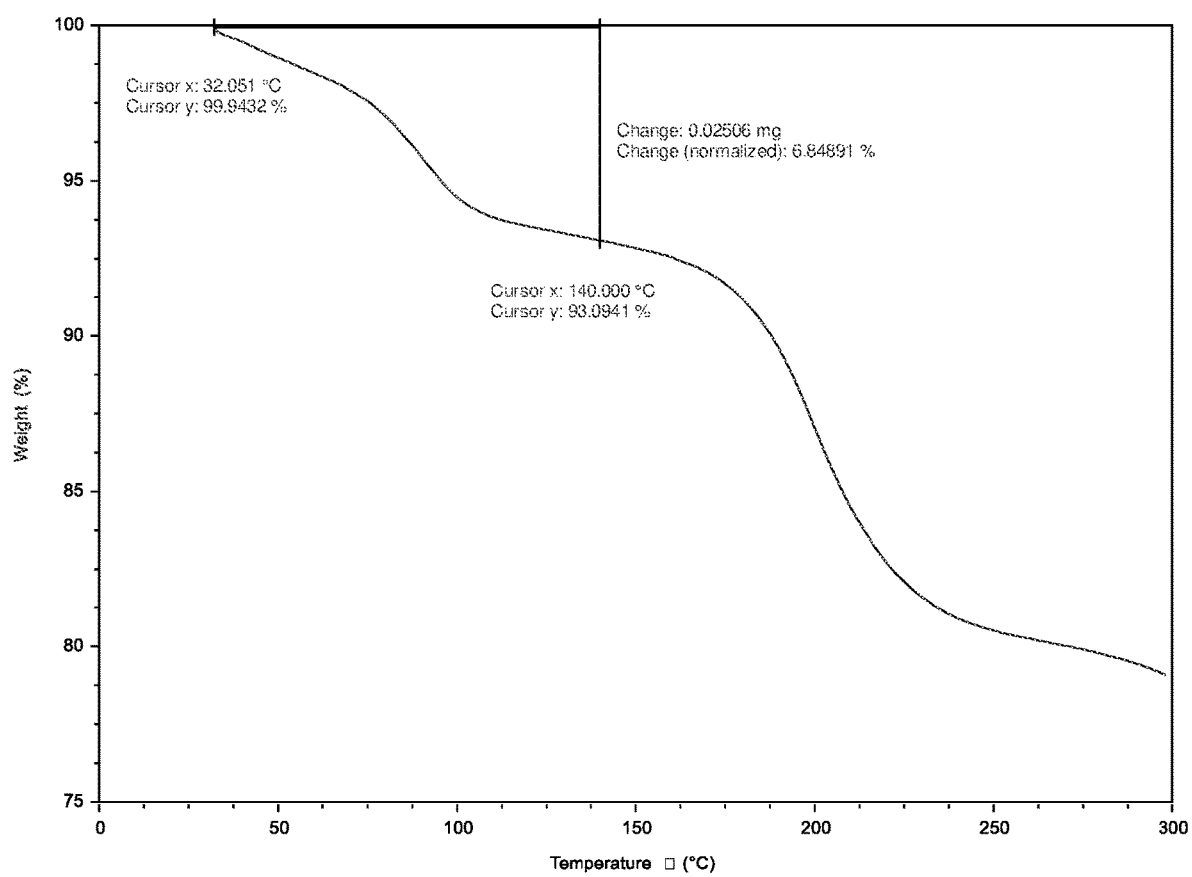
FIG. 18 shows a TGA plot of an X-ray amorphous complex of Compound I and fumaric acid (2:1).

The amorphous Compound I fumaric acid (2:1) is characterized by one or more of the following parameters: (a) an X-ray powder diffraction pattern that is substantially as shown in FIG. 16, showing no well-defined peaks when measured with a CuKα radiation at a wavelength of 0.15 nm at room temperature; (b) a differential scanning calorimetry (DSC) thermogram that is substantially as shown in FIG. 17 when heated from 30 to 300° C. at a rate of 10 K/min; and (c) a thermogravimetric analysis (TGA) diagram that is substantially as shown in FIG. 18 when heated from 30 to 300° C. at a rate of 10 K/min.

Example 7

Stability of Compound I Solid Forms

Compound I, Compound I fumaric acid co-crystals and amorphous Compound I fumaric acid samples (10 mg) were placed in an open vial at 50° C./75% RH and 80° C./75% RH chamber for one week. A same amount of sample was placed in a closed vial at 50° C. and 80° C. chamber for 1 week. The samples were exposed to 100 k Lux light for 12 h at 25° C.

Solids were examined by XRPD for physical stability determination and by UPLC for chemical stability determination. The color of the samples was evaluated by visual observation. Table 5 compares the stability of Compound I and its various solid forms.

At initial purity, the Compound I free form is a hydrate, which changes into a dihydrate when stored at 92% RH and after DVS testing. The free form hydrate converts to an amorphous form after degradation at 160° C. The free form hydrate is chemically stable in bulk at 50° C., 50° C./75& RH, 80° C. and 80° C./75% RH for one week, but form changes were noticed. Upon exposure to 75% RH humidity at both temperatures, a dihydrate was obtained. A mixture of the free form hydrate and anhydrous modification was observed under 50° C./75% RH. The free form is stable upon exposure to 1200 kLuxh light for 12 hrs.

The free form hydrate is hygroscopic with 8.9% moisture absorption by DVS at 25° C., along with a form change that is likely a dihydrate. The dihydrate is also obtained after storage of the free form hydrate at 92% RH for 24 hrs. After grinding, compression and wet granulation with water and ethanol, the free form hydrate converted to a different hydrate or a hydrate mixture.

In contrast, Form B and Compound I fumaric acid co-crystals (2:1) are non-hygroscopic and remains the same form with 0.3% and 0.12% moisture absorption respectively at 90% RH by DVS. Grinding, compression and wet granulation did not alter the crystal form of Form B.

TABLE 5

| | Free Form | | Form B | | Form C | | Compound I Fumaric Acid Co-crystal (2:1) | | Amorphous Compound I Fumaric Acid (1:1) | | Amorphous Compound I Fumaric Acid (2:1) | |
|---|---|---|---|---|---|---|---|---|---|---|---|---|
| | DP % | CL | DP % | CL | DP % | CL | DP % | CL | DP % | CL | DP % | CL |
| Initial purity | 99.4 (hydrate) | off-white powder | 98.2 | off-white powder | 98.1 | light yellow powder | 98.8 | off-white powder | 97.4 | off-white powder | 98.7 | white powder |
| *Solid state, 1 week 80° C., closed container* | | | | | | | | | | | | |
| Bulk (UPLC) | 0.6 | no change | 1.7 | no change | 1.8 | no change | 1.2 | no change | 2.6 | no change | 1.7 | no change |
| Bulk (XRPD) | no change | | no change | | no change | | no change | | no change | | no change | |
| *Solid state, 1 week 80° C./75% r.h.* | | | | | | | | | | | | |
| Bulk (UPLC) | 0.6 | no change | 1.7 | no change | 1.8 | no change | 1.2 | no change | 2.7 | no change | 1.6 | no change |
| Bulk (XRPD) | no change | | no change | | no change | | no change | | very weak crystallinity | | no change | |
| *Solid state, 1 week 50° C., closed container* | | | | | | | | | | | | |
| Bulk (UPLC) | 0.6 | no change | 1.8 | no change | 1.8 | no change | 1.2 | no change | ND | | ND | |
| Bulk (XRPD) | no change | | no change | | no change | | no change | | ND | | ND | |
| *Solid state, 1 week 50° C./75% r.h.* | | | | | | | | | | | | |
| Bulk (UPLC) | 0.6 | no change | 1.7 | no change | 1.7 | no change | 1.2 | no change | ND | | ND | |
| Bulk (XRPD) | no change | | no change | | no change | | no change | | ND | | ND | |
| *Xenon light (approx. 1200 kLuxh)* | | | | | | | | | | | | |
| Clear vial (HPLC) | 0.6 | no change | 1.6 | no change | 1.8 | no change | 1.2 | no change | 4.5 | no change | 10.6 | no change |
| Clear vial (XRPD) | no change | | no change | | no change | | no change | | very weak crystallinity | | crystallized | |
| Amber vial (HPLC) | 0.8 | no change | 1.7 | no change | 1.8 | no change | 1.2 | no change | 2.8 | no change | 1.5 | no change |
| Amber vial (XRPD) | no change | | no change | | no change | | no change | | very weak crystallinity | | crystallized | |

*ND (not determined);
DP (Degradation Product);
CL (color)

Example 8

Solubility of Compound I Solid Forms

Compound 1, Compound I fumaric acid co-crystals and amorphous Compound I fumaric acid samples (2 mg) in various media (1 mL) were mixed in a glass vial to make a slurry. Each sample was equilibrated at 2500 for 24 hrs, and centrifuged at 13400 r.p.m. for 3 mins with 0.2 μm membrane to separate solids from liquids. The liquid was used to measure solubility by UPLC.

Table 6 provides solubility data of Compound I and its various solid forms at 25° C. after 24 hours equilibration, with final pH of the sample shown in parentheses. The solubility of Form B in biological fluids such as SGF, FaSSIF and FeSSIF was significantly better compared to the solubility of the free form. The solubility of Compound I fumaric acid co-crystal (2:1) in FeSSIF was also significantly better compared to the solubility of the free form.

TABLE 6

|  | Free Form (mg/mL) | Form B (mg/mL) | Form C (mg/mL) | Compound I Fumaric Acid Co-crystal (2:1) (mg/mL) | Amorphous Compound I Fumaric Acid (1:1) (mg/mL) | Amorphous Compound I Fumaric Acid (2:1) (mg/mL) |
|---|---|---|---|---|---|---|
| water | 0.009 (8.18) | 0.004 (2.9) | ND (2.9) | ND (3.1) | 0.0002 (3.0) | <0.0001 (3.2) |
| 0.1N HCl pH 1.0 | 0.232 (1.00) | 0.17 (1.0) | 0.24 (1.1) | 0.16 (0.8) | 0.35 (1.1) | 0.18 (1.1) |
| 0.01N HCl pH 2.0 | 0.017 (2.10) | 0.021 (2.1) | // | 0.005 (1.9) | 0.036 (2.1) | 0.009 (2.0) |
| acetate buffer pH 4.7 | 0.002 (4.68) | 0.002 (4.6) | ND (4.4) | ND (4.5) | <0.0001 (4.6) | <0.0001 (4.7) |
| phosphate buffer pH 6.8 | 0.001 (6.65) | 0.002 (6.5) | ND (6.4) | ND (6.6) | <0.0001 (6.6) | <0.0001 (6.7) |
| borate buffer pH 10.0 | 0.002 (8.58) | 0.002 (8.1) | // | ND (9.6) | <0.0001 (9.6) | <0.0001 (9,7) |
| SGF pH 2.0 | 0.029 (1.99) | 0.063 (1.9) | 0.046 (2.0) | 0.03 (1.9) | 0.055 (2.2) | 0.025 (2.2) |
| FaSSIF pH 6.5 | 0.004 (6.31) | 0.007 (5.7) | ND (5.5) | ND (5.9) | 0.007 (5.8) | 0.003 (6.1) |
| FeSSIF pH 5.8 | 0.006 (5.73) | 0.016 (5.6) | ND (5.5) | 0.017 (5.5) | 0.018 (5.6) | 0.013 (5.7) |

*ND (not determined)

Having fully described the invention, it will be understood by persons of skill in the art that the same can be performed within various modifications without affecting the scope of the invention or any embodiment thereof. All publications, patents, and patent applications cited herein are hereby incorporated by reference for all purposes.

The invention claimed is:

1. A co-crystal comprising N-(4-fluoro-3-(6-(3-methylpyridin-2-yl)[2,4]triazolo[1,5- a]pyrimidin-2-yl)phenyl)-2,4-dimethyloxazole-5-carboxamide and fumaric acid; wherein said co-crystal is characterized by:
   (i) an X-ray powder diffraction pattern comprising three or more 2θ peaks selected from 24.7°±0.2°, 23.9°±0.2°, 16.0°±0.2° (2θ) and 13.4°±0.2° (2θ);
   (ii) an X-ray powder diffraction pattern comprising three or more three or more 2θ peaks selected from 27.6°±0.2°, 14.8°±0.2°, 9.8°±0.2°, 11.3°±0.2°, 24.6°±0.2°, 25.0°±0.2° and 26.5°±0.2° (2θ); or
   (iii) an X-ray powder diffraction pattern comprising three or more 2θ peaks selected from 13.5°±0.2°, 3.8°±0.2°, 17.2°±0.2°and 26.6°±0.2 (2θ);
   when measured with a CuKα radiation at a wavelength of 0.15 nm at room temperature.

2. The co-crystal of claim 1, having an X-ray powder diffraction pattern comprising 2θ peaks at 24.7°±0.2°, 23.9°±0.2° and 16.0±0.2.

3. The co-crystal of claim 1, which is characterized by one of more selected from: (a) an X-ray powder diffraction pattern that is substantially as shown in FIG. 4 when measured with a CuKα radiation at a wavelength of 0.15 nm; (b) a differential scanning calorimetry (DSC) thermogram that is substantially as shown in FIG. 5 when heated from 30 to 300° C. at a rate of 10 K/min; and (c) a thermogravimetric analysis (TGA) diagram that is substantially as shown in FIG. 6 when heated from 30 to 300° C. at a rate of 10 K/min.

4. The co-crystal of claim 1, having an X-ray powder diffraction pattern comprising 2θ peaks at 27.6°±0.2°, 14.8°±0.2°, and 9.8°±0.2° (2θ).

5. The co-crystal of claim 1, which is characterized by one of more selected from: (a) an X-ray powder diffraction pattern that is substantially as shown in FIG. 7 when measured with a CuKα radiation at a wavelength of 0.15 nm; (b) a differential scanning calorimetry (DSC) thermogram that is substantially as shown in FIG. 8 when heated from 30 to 300° C. at a rate of 10 K/min; and (c) a thermogravimetric analysis (TGA) diagram that is substantially as shown in FIG. 9 when heated from 30 to 300° C. at a rate of 10 K/min.

6. The co-crystal of claim 1, having an X-ray powder diffraction pattern comprising 2θ peaks at 13.5°±0.2°, 3.8°±0.2° and 17.2°±0.2° (2θ).

7. The co-crystal according to claim 1, which is characterized by one of more selected from: (a) an X-ray powder diffraction pattern that is substantially as shown in FIG.10 when measured with a CuKα radiation at a wavelength of 0.15 nm; (b) a differential scanning calorimetry (DSC) thermogram that is substantially as shown in FIG. 11 when heated from 30 to 300° C. at a rate of 10 K/min; and (c) a thermogravimetric analysis (TGA) diagram that is substantially as shown in FIG. 12 when heated from 30 to 300° C. at a rate of 10 K/min.

8. A composition comprising the co-crystal according to claim 1.

9. The composition according to claim 8, comprising at least 90% by weight of said co-crystal based on the weight of the composition.

10. The composition according to claim 9, comprising at least 80% by weight of said co-crystal based on the weight of the composition.

11. A pharmaceutical composition comprising the co-crystal according to claim 1 and a pharmaceutically acceptable carrier.

12. A combination comprising the co-crystal according to claim 1, and one or more therapeutically active agents.

13. A process for preparing a co-crystal according to claim 1, comprising (1) adding fumaric acid to a first solvent to form a fumaric acid solution; (2) adding N-(4-fluoro-3-(6-(3-methylpyridin-2-yl)-[1,2,4]triazolo[1,5-a]pyrimidin-2-yl) phenyl)-2,4-dimethyloxazole-5-carboxamide to a second solvent to form a N-(4-fluoro-3-(6-(3-methylpyridin-2-yl)-[1,2,4]triazolo[1,5-a]pyrimidin-2-yl) phenyl)-2,4-dimethyloxazole-5-carboxamide solution; and (3) adding said N-(4-fluoro-3-(6-(3-methylpyridin-2-yl)[1,2,4]triazolo[1,5-a]pyrimidin-2-yl)phenyl)-2,4-dimethyloxazole-5-carboxamide solution to said fumaric acid solution under suitable conditions to form said N-(4-fluoro-3-(6-(3-methylpyridin-2-yl)[1,2,4]triazolo[1,5-a]pyrimidin-2-yl)phenyl)-2,4-dimethyloxazole-5-carboxamide fumaric acid co-crystal.

14. A process for preparing a co-crystal according to claim 1, comprising (1) adding fumaric acid to a first solvent to form a fumaric acid solution; (2) adding N-(4-fluoro-3-(6-(3-methylpyridin-2-yl)-[1,2,4]triazolo[1,5-a]pyrimidin-2-yl) phenyl)-2,4-dimethyloxazole-5-carboxamide to a second solvent to form a N-(4-fluoro-3-(6-(3-methylpyridin-2-yl)-[1,2,4]triazolo[1,5-a]pyrimidin-2-yl) phenyl)-2,4-dimethyloxazole-5-carboxamide solution; and (3) adding said fumaric acid solution to said N-(4-fluoro-3-(6-(3-methylpyridin-2-yl)-[1,2,4]triazolo[1,5-a]pyrimidin-2-yl) phenyl)-2,4-dimethyloxazole-5-carboxamide solution to form said N-(4-fluoro-3-(6-(3-methylpyridin-2-yl)[1,2,4]triazolo[1,5-a]pyrimidin-2-yl)phenyl)-2,4-dimethyloxazole-5-carboxamide fumaric acid co-crystal.

* * * * *